(12) United States Patent
Hueter et al.

(10) Patent No.: US 11,369,113 B2
(45) Date of Patent: Jun. 28, 2022

(54) VECTOR CONTROL COMPOSITIONS, METHODS AND PRODUCTS UTILIZING SAME

(71) Applicant: Syngenta Participations AG, Basel (CH)

(72) Inventors: Ottmar Franz Hueter, Stein (CH); Mark Hoppe, Stein (CH); Tomas Smejkal, Stein (CH); Raphael Dumeunier, Stein (CH); Nicolas Fedou, Münchwilen (CH); Edouard Godineau, Stein (CH); Philip Wege, Bracknell (GB); Peter Maienfisch, Basel (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/759,147

(22) PCT Filed: Oct. 24, 2018

(86) PCT No.: PCT/EP2018/079148
§ 371 (c)(1),
(2) Date: Apr. 24, 2020

(87) PCT Pub. No.: WO2019/081575
PCT Pub. Date: May 2, 2019

(65) Prior Publication Data
US 2020/0315175 A1    Oct. 8, 2020

(30) Foreign Application Priority Data
Oct. 27, 2017 (EP) ..................................... 17198806

(51) Int. Cl.
*A01N 43/78* (2006.01)
*C07D 277/34* (2006.01)

(52) U.S. Cl.
CPC ........... *A01N 43/78* (2013.01); *C07D 277/34* (2013.01)

(58) Field of Classification Search
CPC ............................. A01N 43/78; C07D 277/34
USPC ........................................................ 514/369
See application file for complete search history.

(56) References Cited

FOREIGN PATENT DOCUMENTS

| EP | 0192148 A1 * | 8/1986 | ........... C07D 277/32 |
|---|---|---|---|
| EP | 0192148 A1 | 8/1986 | |
| WO | 2012089606 A1 | 7/2012 | |
| WO | 2016193267 A1 | 12/2016 | |
| WO | WO-2016193267 A1 * | 12/2016 | ........... C07D 241/18 |

OTHER PUBLICATIONS

International Search Report and Written Opinion for International Application PCT/EP2018/079148 dated Feb. 25, 2019.
Partial Search result for PCT/EP2018/079148, dated Dec. 4, 2018.
Extended ESR for EP17198806.6, dated Apr. 17, 2018.
Partial ESR for EP17198806.6, dated Jan. 3, 2018.

* cited by examiner

*Primary Examiner* — Timothy R Rozof
(74) *Attorney, Agent, or Firm* — BakerHostetler; Toni-Junell Herbert

(57) ABSTRACT

The present inventions concerns use of a specific methoxyacrylate compound to control mosquitoes, and vector control products comprising that methoxyacrylate compound, in particular the invention relates to a substrate, to a composition, for controlling mosquitoes, and to a specific methoxyacrylate compound, processes for the synthesis of mosquitocidal methoxyacrylate compounds and new intermediates.

21 Claims, No Drawings

VECTOR CONTROL COMPOSITIONS, METHODS AND PRODUCTS UTILIZING SAME

CROSS-REFERENCE TO RELATED APPLICATIONS

This application is a 371 National Stage application of International Application No. PCT/EP2018/079148, filed Oct. 24, 2018 which claims priority to EP 17198806.6 filed Oct. 27, 2017, the entire contents of which applications are hereby incorporated by reference.

The present invention is in the technical field of vector control, particular insect vector control, such as mosquitos, with a defined compound of formula I. More specifically, the present invention relates to methods of controlling mosquitoes and to substrates, products, compositions and vector control management products for controlling mosquitoes, each comprising a mosquitocidally active compound of formula I.

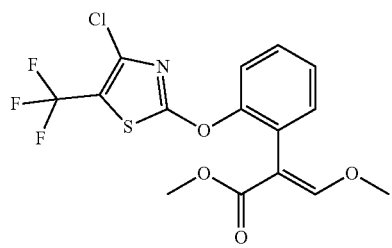

(I)

Mosquito control manages the population of mosquitoes to reduce their damage to human health, economies, and enjoyment. Mosquito control is a vital public-health practice throughout the world and especially in the tropics because mosquitoes spread many diseases, such as malaria (Wikipedia contributors, "Mosquito control", Wikipedia).

Mosquito-control operations are targeted against three different problems:
1. Nuisance mosquitoes bother people around homes or in parks and recreational areas;
2. Economically important mosquitoes reduce real estate values, adversely affect tourism and related business interests, or negatively impact livestock or poultry production;
3. Public health is the focus when mosquitoes are vectors, or transmitters, of infectious disease.

Many infectious diseases (e.g., malaria, dengue and yellow fever, lymphatic filariasis, and leishmaniasis) that are responsible for debilitating or even killing humans and animals in many countries, especially in tropical countries, are transmitted by insect vectors. For example, the mosquito parasite, *Plasmodium falciparum*, accounts for greater than 25 percent of childhood mortality outside the neonatal period. In certain parts of Africa, malaria has been ranked first by the World Bank in terms of disability-adjusted life-years lost. A number of drugs are available to treat and/or prevent some insect-borne diseases. However, not all diseases transmitted by mosquitoes can be treated efficiently. For example, there is currently no chemotherapeutic drug or vaccine available against the Dengue virus. Furthermore, in the case of antimalarial drugs, treatment with the drugs currently available is becoming less effective due to increased resistance in some *Plasmodium* strains. *Plasmodium* enters the human bloodstream as a consequence of the insect bite and causes malaria. Therefore, one of the most effective ways to prevent mosquito vector-borne illnesses is by decreasing mosquito populations in areas of high pathogen transmission and/or preventing mosquito bites in the first place. More recently, efforts have been concentrated on controlling the transmitting mosquitoes.

The three medically important genera of insects which transmit diseases are the mosquitoes *Anopheles, Culex* and *Aedes*. The genera *Culex* and *Aedes* belong to the sub-family Culicinae, while the *Anopheles* belongs to the sub-family Anophelinae.

Examples of diseases or pathogens transferred by the key mosquitoes are:
*Anopheles*: malaria, filariasis;
*Culex*: Japanese encephalitis, other viral diseases, filariasis; and
*Aedes*: yellow fever, dengue fever, chikungunya, other viral diseases (e.g., Zika virus), and filariasis;

In an attempt to reduce the problems associated with disease-transmitting mosquitoes, a wide range of insecticides and insect repellents have been developed. Mosquitoes can be targeted with insecticides when they are in a larval state or once they have developed into adults. Accordingly, insecticides which are used to kill larvae are termed larvicides whereas insecticides that are used to specifically target adult insects are called adulticides. Most of the insecticides commonly used to prevent the spread of disease are targeted against the adult mosquito and in particular against the female adult mosquito.

The organochlorine DDT was the most widespread compound used worldwide as an adulticide until it was withdrawn from use in most areas. After that, organophosphates such as malathion, carbamates, e.g., propoxur were widely used in vector control programmes in most parts of the world and were steadily replaced by pyrethroids, which became the mostly used adulticide. Organophosphates, such as pirimiphos-methyl are now being used again due to the development of pyrethroid resistance in many important vector species.

One of the most important problems associated with pyrethroids, like their predecessors, is that resistance has already developed in many insect species in several parts of the world. Pyrethroid resistance, caused either by specific detoxification enzymes or an altered target site mechanism (kdr-type mutations in the sodium channels), has been reported in most continents in the majority of medically important mosquitoes species, such as *Anopheles gambiae* in Africa and *Aedes aegypti* in Asia. If resistance continues to develop and spread at the current rate, it may render such insecticides ineffective in their current form in the not too distant future. Such a scenario would have potentially devastating consequences in public health terms, since there are as yet no obvious alternatives to many of the uses of pyrethroids.

Therefore, there is an ongoing search for compounds for control of mosquitoes, especially for mosquitoes having developed resistance, such as against pyrethroids. Recently certain methoxyacrylate compounds with activity against mosquitoes were found (WO 2016193267).

With the present invention, it has now been found that a specific compound of formula I showed even better activity against mosquitoes and was surprisingly useful for controlling mosquitoes and for decreasing mosquito vector populations.

The compound of formula I showed surprisingly improved characteristics as a product for mosquito control compared to the structurally closely related compound of formula II published in WO 2016193267, particularly against certain insecticide resistant mosquito species.

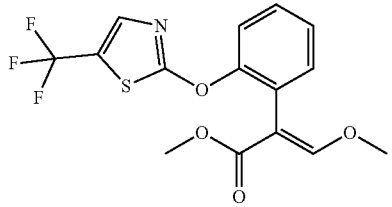
(II)

Accordingly, in a first aspect, the present invention provides a compound of formula I, or a geometric isomer, salt, or a N-oxide thereof.

In a second aspect, the present invention provides for the use of a compound of the first aspect for controlling mosquitoes.

In a third aspect, the present invention provides compositions, products, and treated articles (such as substrates or non-living materials) comprising the compound of the first aspect.

In a fourth aspect, the present invention provides a vector control, preferably a mosquito control, management product comprising the compound of the first aspect.

The compound of the invention may exist in different geometric forms. This invention covers all such isomers and mixtures thereof in all proportions as well as isotopic forms such as deuterated compounds.

The compound of formula I and, where appropriate, a geometric isomer thereof, in each case in free form or in salt form, can be present in the form of one of the isomers which are possible or as a mixture of these, for example in the form of pure isomers or as isomer mixtures; the invention relates to the pure isomers and also to all isomer mixtures which are possible and is to be understood in each case in this sense hereinabove and hereinbelow, even when stereochemical details are not mentioned specifically in each case. This invention accordingly covers all such isomers and mixtures thereof in all proportions as well as isotopic forms such as deuterated compounds.

The invention also covers salts and N-oxides of each compound for formula (I).

One skilled in the art also recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts amongst agriculturally and/or physiologically tolerable salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Suitable amongst agriculturally and/or physiologically tolerable salts can also be the salts of those cations which do not adversely affect the pesticidal and/or parasiticidal action of the compounds of formula (I). Thus, especially suitable cations are the ions of the alkali metals including sodium, potassium and lithium, of the alkaline earth metals including calcium and magnesium, and of the transition metals including manganese, copper, iron, zinc, cobalt, lead, silver, nickel, and also ammonium or organic ammonium including monoalkylammonium, dialkylammonium, trialkylammonium, tetraalkylammonium, monoalkenylammonium, dialkenylammonium, trialkenylammonium, monoalkynylammonium, dialkynyla monium, monoalkanolammonium, dialkanolammonium, C5-C6-cycloalkylammonium, piperidinium, morpholinium, pyrrolidinium, or benzylammonium, moreover phosphonium ions, sulfonium ions, preferably tri(C1-C4-alkyl) sulfonium and sulfoxonium ions, preferably tri (C1-C4-alkyl) sulfoxonium.

The compound of formula I can be prepared by reacting a thiazole compound III containing a leaving group LG1 under basic conditions with a phenol compound IV similar to procedures described in WO 9505368 or EP 242081. LG1 can be a halogen, preferably bromine, fluorine or chlorine, most preferably chlorine or an alkyl sulfonyl group, preferably methylsulfonyl. The base can be a carbonate salt such as $Na_2CO_3$, $K_2CO_3$, $Cs_2CO_3$ more preferably $K_2CO_3$; an alkoxide base such as NaOMe or NaOtBua hydroxide base such NaOH or KOH; a amine base such at $Et_3N$ or $iPr_2NEt$. The reaction can be carried out neat or in a solvent. Preferably the reaction is carried out in a solvent. The solvent can be MeOH, EtOAc, toluene, benzene, pentane, hexane, heptane, acetone, THF, NMP, DMSO or DMF, preferably DMF. The reaction can be performed in the presence of a catalyst, for example a tertiary amine such as dimethylaminopyridine or DABCO, more preferably DABCO. The reaction can be carried out between 0° C. and the boiling point of the used solvent, preferably between 20° C. and 80° C., most preferably at 20° C. and 50° C. (Scheme 1).

Scheme 1

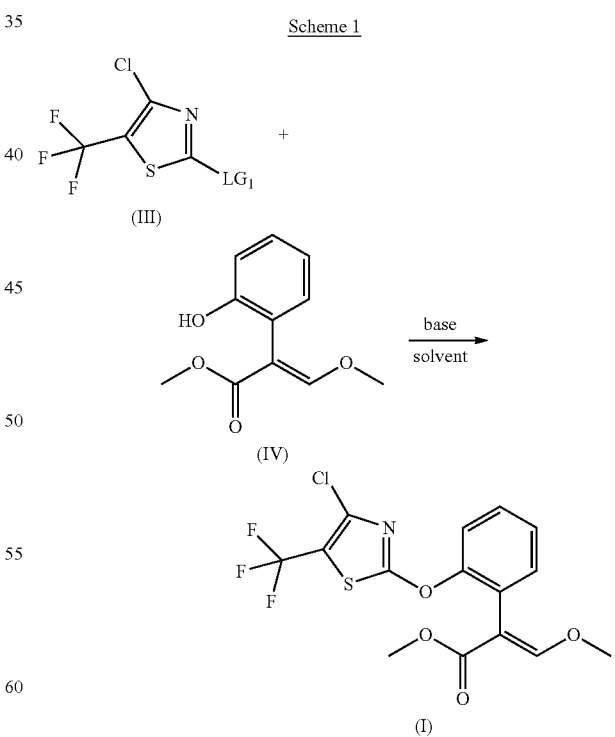

Alternatively the compound of formula I can be prepared similar to procedures published in WO 9807707 by treating an acetal V with an acid, e.g. 0.001 eq to 1 eq methanesulfonic acid, in the presence of acetic anhydride. The reaction can be carried out neat in acetic anhydride or in a solvent. The solvent can be EtOAc, toluene, pentane, hexane, heptane, acetone, THF (tetrahydrofuran), NMP (N-methyl-2-pyrrolidon) or DMF (N,N-dimethylformamide). The reaction can be carried out between 0° C. and the boiling point of the used solvent, preferably between 20° C. and 80° C., most preferably at 50° C. (Scheme 2).

Scheme 2

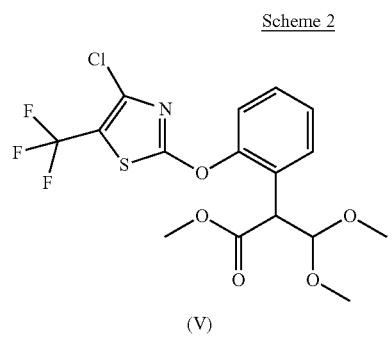

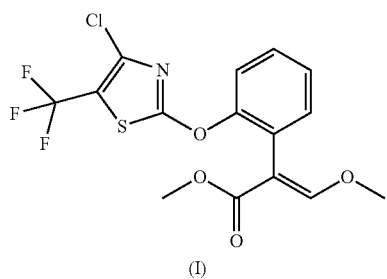

The compound of formula V can be prepared by reacting a thiazole compound III containing a leaving group LG1 under basic conditions with a phenol compound VI similar to procedures published in DE 19525393 (publ. 1996). LG1 can be a halogen, preferably bromine, fluorine or chlorine or an alkyl sulfonyl group, preferably methylsulfonyl. The base can be a carbonate salt such as $Na_2CO_3$, $K_2CO_3$, $Cs_2CO_3$ more preferably $K_2CO_3$; an alkoxide base such as NaOMe or NaOtBu, a hydroxide base such NaOH or KOH; an amine base such at $Et_3N$ or $iPr_2NEt$ The reaction can be carried out neat or in a solvent. Preferably the reaction is carried out in a solvent. The solvent can be MeOH, EtOAc, toluene, benzene, pentane, hexane, heptane, acetone, THF, NMP or DMF, or DMSO; preferably DMF. The reaction can be performed in the presence of a catalyst, for example an amine, preferably DABCO. The reaction can be carried out between 0° C. and the boiling point of the used solvent, preferably between 20° C. and 80° C., most preferably at 20° C. and 50° C. (Scheme 3).

Scheme 3

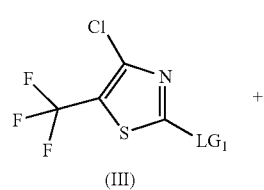

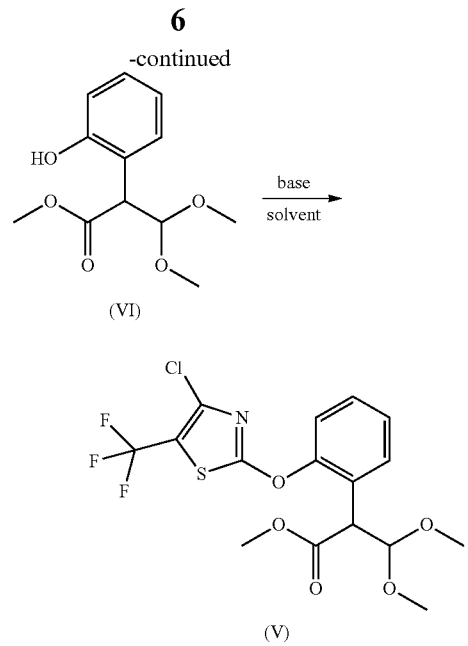

The phenol compound VI is a known compound and can be synthesized in 2 steps starting from 3H-benzofuran-2-one according to procedures published in U.S. Pat. No. 5,760,250 (publ. 1998) and DE 19525393 (publ. 1996).

The thiazole compound IIIa (with LG1=Cl) is a known compound and can be synthesized in 3 steps (Scheme 4) starting from 5-methyl-2,4-thiazolidinedione VII according to procedures published by Bayer in DE 3505900 (publ. 1986) and DE 3505902 (publ. 1986). According to DE 3505900 and DE 3505902 the compound IIIa was formed by fluorination of compound IX with dry hydrogenfluoride.

Alternatively compound IIIa can be formed by fluorination of compound IX with HF.pyridine or other fluorination reagents. The reaction can be carried out at elevated temperature between 50° C. and 250° C., preferably between 80° C. and 150° C. under pressure.

Scheme 4

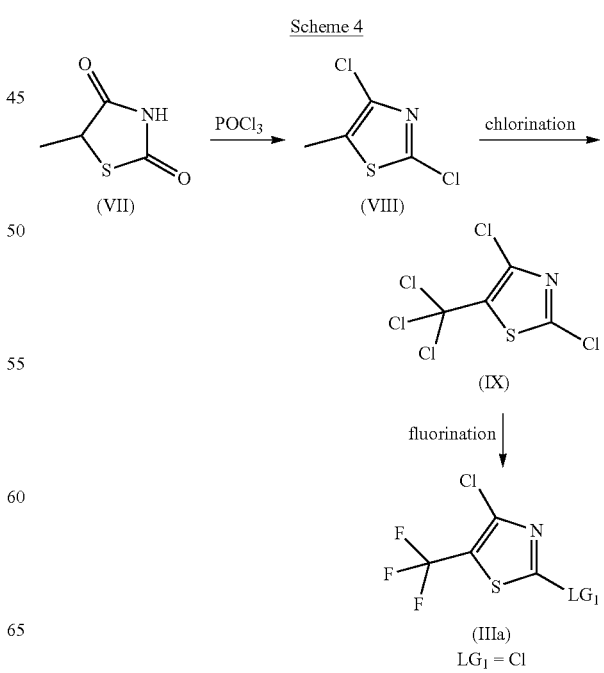

Under certain fluorination conditions the thiazole IIIb might be formed.

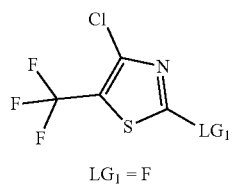

LG₁ = F

Alternatively the thiazole compound IX can be synthesized starting from 2-chloro-5-(chloromethyl) thiazole X (Scheme 5). 2-chloro-5-(chloromethyl)thiazole X can be chlorinated with a suitable chlorination reagent, for example Cl₂ or SO₂Cl₂. The reaction can be carried out neat at higher temperature between 100° C. and 250° C., preferably between 160° C. and 240° C. The reaction might be performed under pressure. It can be advantageous to add a radical initiator, for example benzoylperoxide or azobisisobutyronitrile (AIBN). The resulting pentachlorothiazole compound IX can be fluorinated with a suitable fluorination reagent, for example water-free HF or pyridine-HF (most preferably in neat HF or neat Pyr.HF, at temperatures between 50 and 250° C.). (Scheme 4).

Scheme 5

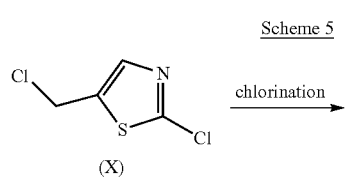

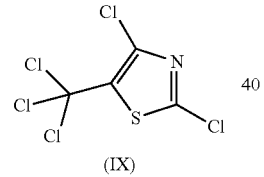

In a further aspect of the present invention, compound of the formula V and a compound of the formula IX is made available.

Further aspects of the present invention include:
a process for making a compound of formula I of the first aspect comprising
  (a) reacting the thiazole compound III containing a leaving group LG1 under basic conditions with the phenol compound IV in a solvent in the presence of an amine catalyst at a temperature between 0° C. and the boiling point of the solvent;

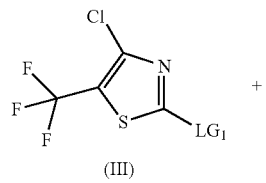

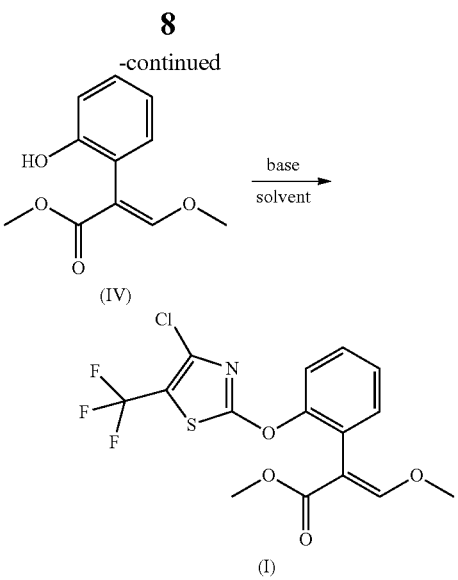

or
(b) treating the acetal compound V with an acid in the presence of acetic anhydride in a solvent between 0° C. and the boiling point of the used solvent.

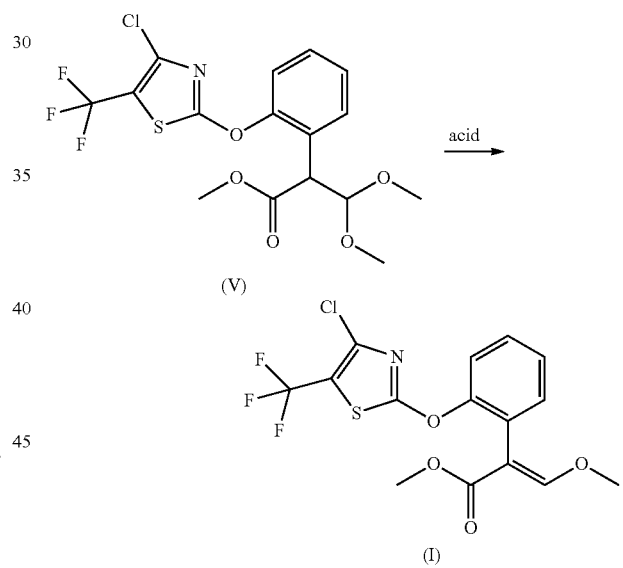

a process for making a compound of formula V comprising reacting a thiazole compound III containing a leaving group LG1 under basic conditions with a phenol compound VI in a solvent in the presence of a catalyst between 0° C. and the boiling point of the used solvent.

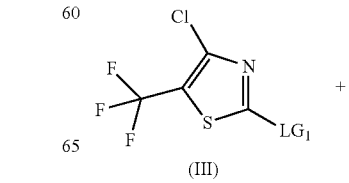

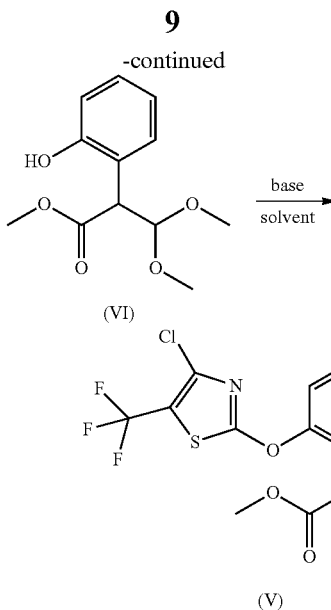

process for making a compound of formula IIIa comprising fluorination of compound IX with HF.pyridine or other fluorination reagents (excluding hydrogenfluoride) at elevated temperature between 50° C. and 250° C. under pressure.

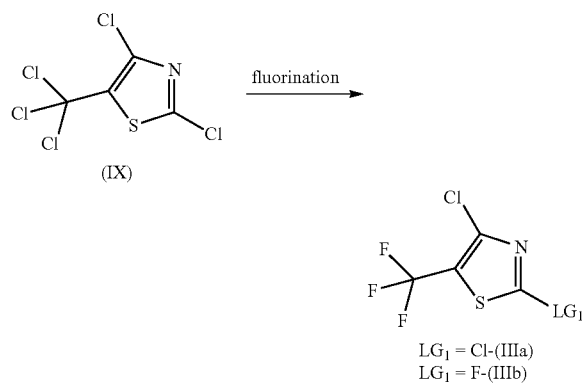

and
process for making a compound of formula IX comprising chlorinating 2-chloro-5-(chloromethyl)thiazole X with a suitable reagent at higher temperature between 100° C. and 250° C.

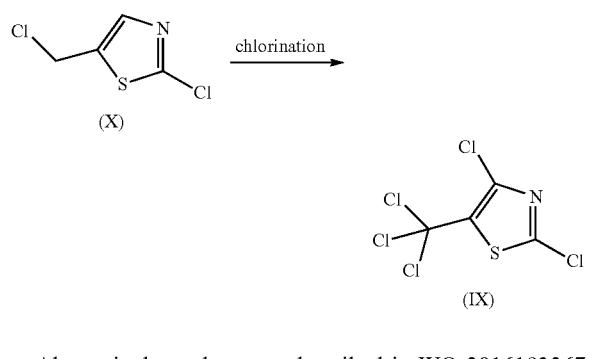

Alternatively to the route described in WO 2016193267 the compound of formula II can be prepared by hydrogenation and removal of a chlorine atom in the thiazole ring of the compound of formula I. The hydrogenation can be carried out with a suitable reducing reagent, for example hydrogen, sodium formate or ammonium formate in the presence of a catalyst, for example palladium, platinum, palladium on activated charcoal, platinum on activated charcoal, or bismuth on activated charcoal. The reaction can be called out neat or in a suitable solvent, for example water, methanol, ethanol, isopropanol, butanol, ethylacetate or in a mixture of two to three of these solvents. The reaction can be carried out at temperatures between 10° C. and 150° C., preferably between 20° C. and 80° C., (Scheme 6).

Scheme 6

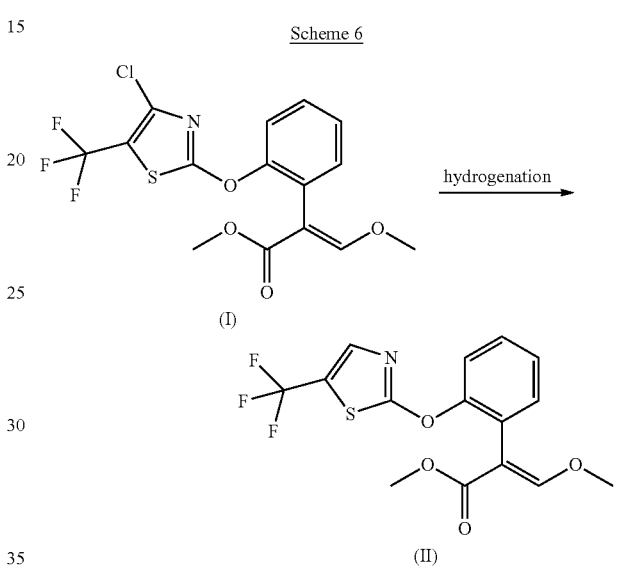

Alternatively to the route described in WO 2016193267 the compound of formula II can be prepared by reacting a thiazole compound XI containing a leaving group LG1 under basic conditions with a phenol compound IV similar to procedures described in WO 9505368 or EP 242081. LG1 can be a halogen, preferably bromine, fluorine or chlorine, most preferably chlorine or an alkyl sulfonyl group, preferably methylsulfonyl. The base can be a carbonate salt such as $Na_2CO_3$, $K_2CO_3$, $Cs_2CO_3$ more preferably $K_2CO_3$; an alkoxide base such as NaOMe or NaOtBu, a hydroxide base such NaOH or KOH; an amine base such at $Et_3N$ or $iPr_2NEt$. The reaction can be carried out neat or in a solvent. Preferably the reaction is carried out in a solvent. The solvent can be MeOH, EtOAc, toluene, benzene, pentane, hexane, heptane, acetone, THF, NMP or DMF, or DMSO; preferably DMF. The reaction can be performed in the presence of a catalyst, for example an amine, preferably DABCO. The reaction can be carried out between 0° C. and the boiling point of the used solvent, preferably between 20° C. and 80° C., most preferably at 20° C. and 50° C. (Scheme 7).

Scheme 7

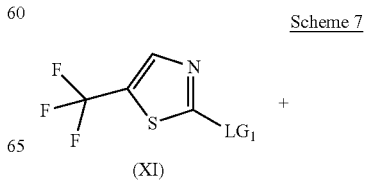

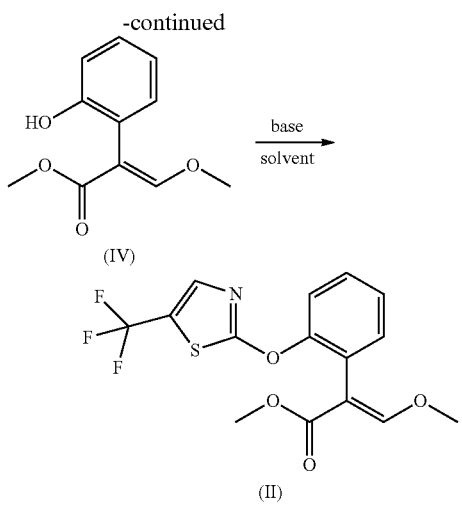

Alternatively to the route described in WO 2016193267 the compound of formula II can be prepared similar to procedures published in WO 9807707 by treating an acetal XII with an acid, e.g. 0.001 eq to 1 eq methanesulfonic acid, in the presence of acetic anhydride. The reaction can be carried out neat in acetic anhydride or in a solvent. The solvent can be EtOAc, toluene, xylene, chlorobenzene, pentane, hexane, heptane, acetone, THF (tetrahydrofuran), NMP (N-methyl-2-pyrrolidon), 2-methyl-tetrahydrofuran, 4-methyl-tetrahydropyran or DMF (N,N-dimethylformamide) The reaction can be carried out between 0° C. and the boiling point of the used solvent, preferably between 20° C. and 80° C., most preferably at 50° C. (Scheme 8).

Scheme 8

The compound of formula XII can be prepared by hydrogenation and removal of a chlorine atom in the thiazole ring of the compound of formula V. The hydrogenation can be carried out with a suitable hydrogenation reagent, for example hydrogen, sodium formate or ammonium formate in the presence of a catalyst, for example palladium, platinum, palladium on activated charcoal, platinum on activated charcoal, or bismuth on activated charcoal. The reaction can be carried out neat or in a suitable solvent, for example water, methanol, ethanol, isopropanol, butanol, ethylacetate or in a mixture of two to three of these solvents. The reaction can be carried out at temperatures between 0° C. and 150° C., preferably between 20° C. and 80° C. (Scheme 9).

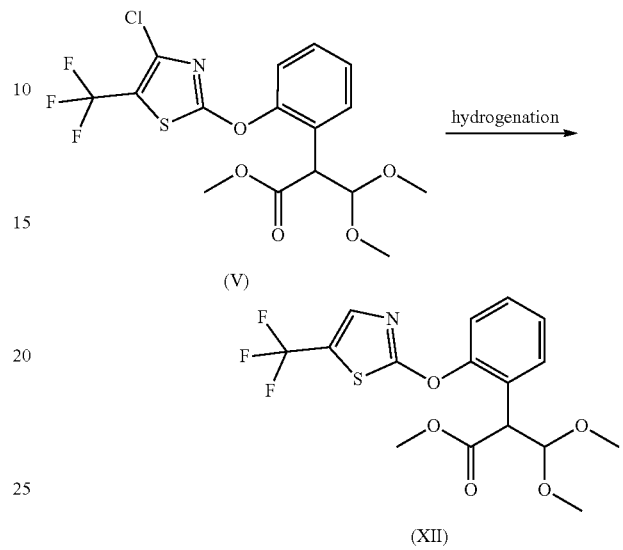

Scheme 9

Alternatively the compound of formula XII can be prepared by reacting a thiazole compound XI containing a leaving group LG1 under basic conditions with a phenol compound VI similar to procedures published in DE 19525393 (publ. 1996). LG1 can be a halogen, preferably bromine or chlorine, most preferably chlorine or an alkyl sulfonyl group, preferably methylsulfonyl. The base can be a carbonate salt such as $Na_2CO_3$, $K_2CO_3$, $Cs_2CO_3$ more preferably $K_2CO_3$; an alkoxide base such as NaOMe or NaOtBu, a hydroxide base such NaOH or KOH; an amine base such at $Et_3N$ or $iPr_2NEt$. The reaction can be carried out neat or in a solvent. Preferably the reaction is carried out in a solvent. The solvent can be MeOH, EtOAc, toluene, benzene, pentane, hexane, heptane, acetone, THF, NMP or DMF, or DMSO; preferably DMF. The reaction can be performed in the presence of a catalyst, for example an amine, preferably DABCO. The reaction can be carried out between 0° C. and the boiling point of the used solvent, preferably between 20° C. and 80° C., most preferably at 20° C. and 50° C. (Scheme 10).

Scheme 10

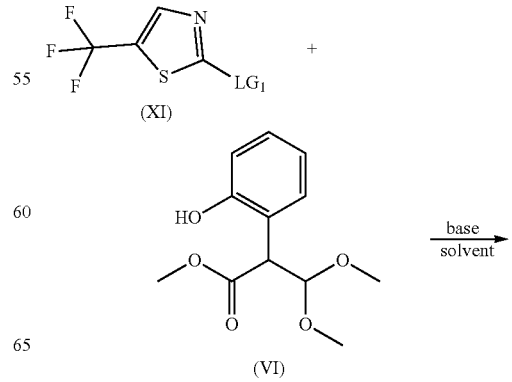

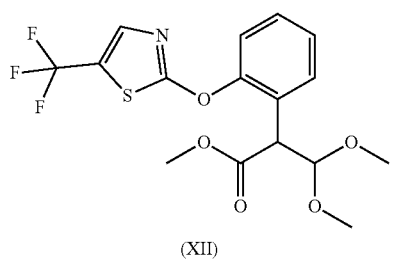

(XII)

The thiazole compound XIa (with LG1=Cl) is a known compound and can be synthesized in a multistep synthesis according to procedures published by Glaxo in WO 2012089606.

Alternatively the thiazole compound XIa (with LG1=Cl) can be synthesized by fluorination of 2-chloro-5-(trichloromethyl)thiazole XIII with a suitable fluorination reagent, for example water-free HF, triethylamine-HF or pyridine-HF (Scheme 11).

Scheme 11

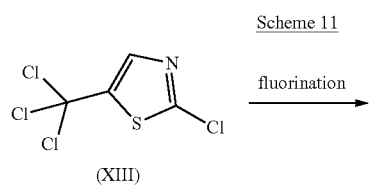

LG$_1$ = Cl

Under certain fluorination conditions the thiazole XIb might be formed.

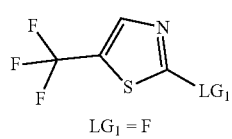

LG$_1$ = F

2-Chloro-5-(trichloromethyl)thiazole XIII can be obtained by chlorination of 2-chlorothiazole-5-carboxylic acid XIV with a suitable chlorination agent, for example phosphorus pentachloride. The reaction may be carried out neat or in a suitable solvent. The reaction can be carried out at temperatures between 100° C. and 250° C. The 2-chlorothiazole-5-carboxylic acid XIV can be first transformed with a different chlorination reagent, for example oxallylchloride or thionylchloride into the corresponding acid chloride XV which can be chlorinated subsequently with a chlorination reagent, for example phosphorus pentachloride (Scheme 12).

Scheme 12

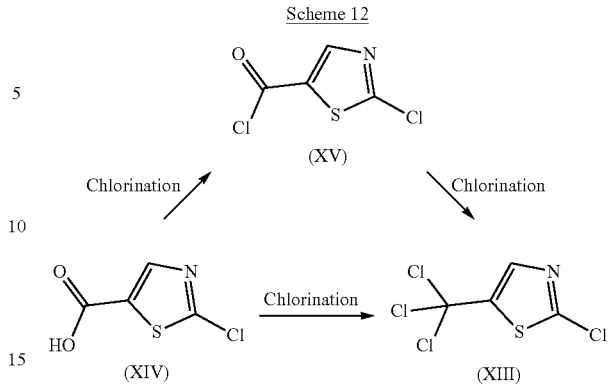

2-chlorothiazole-5-carboxylic acid XIV is a known compound and can be prepared in a multistep synthesis as described for example by Hangzhou Bensheng Pharmaceutical in WO 2012031563.

Alternatively 2-chlorothiazole-5-carboxylic acid XIV can be obtained by oxidation of 2-chloro-5-(chloromethyl)thiazole X, (2-chlorothiazol-5-yl)methanol XVI or 2-chlorothiazole-5-carbaldehyde XVII (see Scheme 13). Suitable oxidation reagents can be $H_2SO_4/HNO_3$ at elevated temperatures between 100° C. and 200° C. or oxone in a suitable solvent, for example $H_2O$ and/or MeCN, or NaOCl in water under neutral or acidic conditions, or oxygen in the presence of a catalyst, for example palladium; preferably $H_2SO_4/HNO_3$ is used at elevated temperatures between 80° C. and 120° C.

Scheme 13

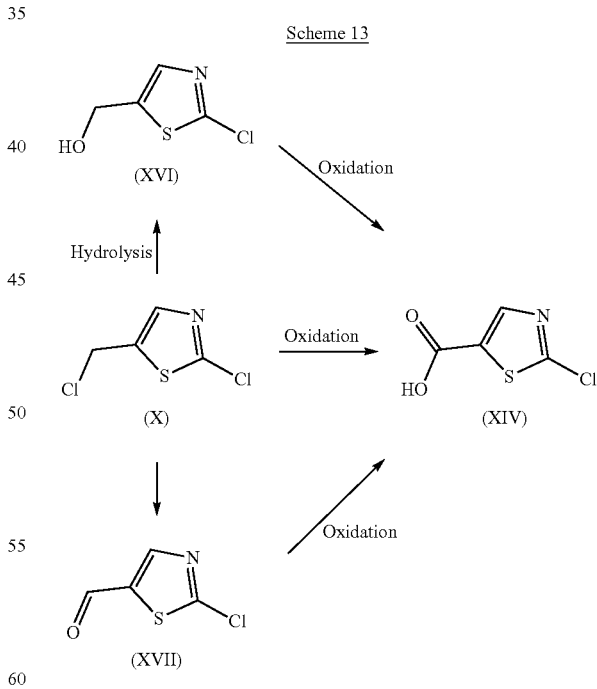

(2-chlorothiazol-5-yl)methanol XVI is a known compound and can be prepared for example by hydrolysis of 2-chloro-5-(chloromethyl)thiazole X as described by Abbott Laboratories in WO 199616050 and WO 199911636.

2-Chlorothiazole-5-carbaldehyde XVII is a known compound and can be prepared for example by reaction of 2-chloro-5-(chloromethyl)thiazole X with hexamethylenetetramine as described by Shandong Dyne Marine Organism Pharmaceutical in CN 105254621 (2016).

Compound of formula XVIII was published in WO 2016193267.

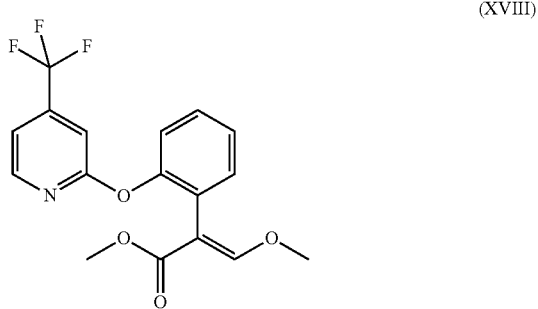 [SMILES: CO/C=C(/C(=O)OC)c1ccccc1Oc1cc(C(F)(F)F)ccn1]

(XVIII)

Compound of formula XVIII can be prepared by hydrogenation and removal of a chlorine atom in the pyridiyl ring of the compound of formula XIX. The hydrogenation can be carried out with a suitable reducing reagent, for example hydrogen, sodium formate or ammonium formate in the presence of a catalyst, for example palladium, platinum, palladium on activated charcoal, platinum on activated charcoal, or bismuth on activated charcoal. The reaction can be carried out neat or in a suitable solvent, for example water, methanol, ethanol, isopropanol, butanol, ethylacetate or in a mixture of two to three of these solvents. The reaction can be carried out at temperatures between 10° C. and 150° C., preferably between 20° C. and 80° C. (Scheme 14).

Scheme 14

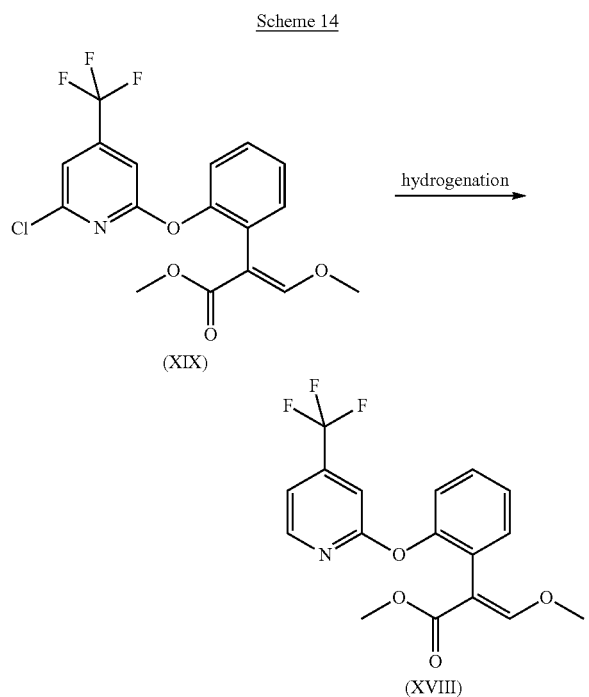

The compound of formula XIX can be prepared similar to procedures published in WO 9807707 by treating an acetal XX with an acid, e.g. 0.001 eq to 1 eq methanesulfonic acid, in the presence of acetic anhydride. The reaction can be carried out neat in acetic anhydride or in a solvent. The solvent can be EtOAc, toluene, xylene, chlorobenzene, pentane, hexane, heptane, acetone, THF (tetrahydrofuran), NMP (N-methyl-2-pyrrolidon), 2-methyl-tetrahydrofuran, 4-methyl-tetrahydropyran or DMF (N,N-dimethylformamide). The reaction can be carried out between 0° C. and the boiling point of the used solvent, preferably between 20° C. and 80° C., most preferably at 50° C. (Scheme 15).

Scheme 15

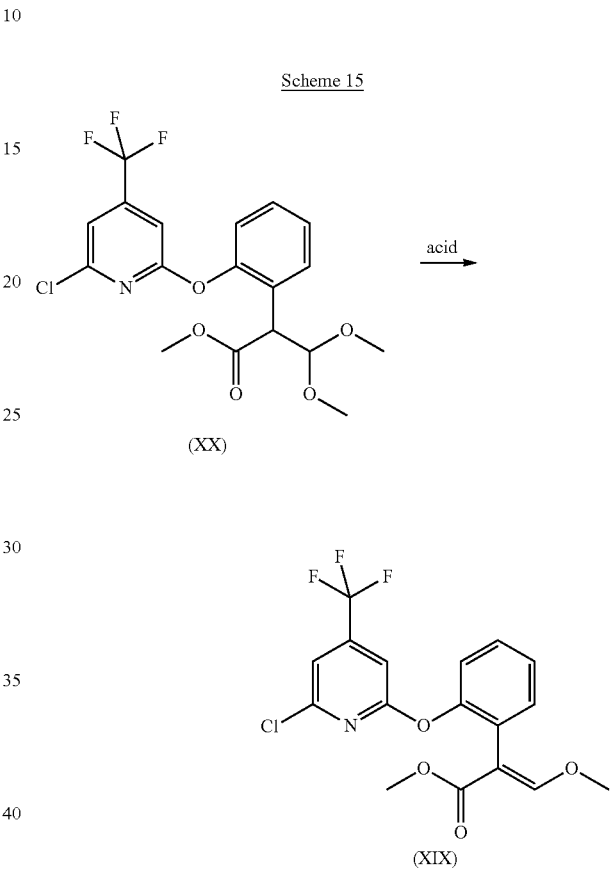

Compound of formula XX can be prepared by reacting a pyridine compound XXI containing a leaving group LG1 under basic conditions with a phenol compound VI similar to procedures published in DE 19525393 (publ. 1996). LG1 can be a halogen, preferably fluorine or chlorine, most preferably chlorine or an alkyl sulfonyl group, preferably methylsulfonyl. The base can be a carbonate salt such as $Na_2CO_3$, $K_2CO_3$, $Cs_2CO_3$ more preferably $K_2CO_3$; an alkoxide base such as NaOMe or NaOtBu, a hydroxide base such NaOH or KOH; an amine base such at $Et_3N$ or $iPr_2NEt$. The reaction can be carried out neat or in a solvent. Preferably the reaction is carried out in a solvent. The solvent can be MeOH, EtOAc, toluene, benzene, pentane, hexane, heptane, acetone, THF, NMP DMF, dimethylacetamide, or DMSO; preferably DMF. The reaction can be performed in the presence of a catalyst, for example an amine, preferably DABCO. The reaction can be carried out between 0° C. and the boiling point of the used solvent, preferably between 20° C. and 80° C., most preferably at 20° C. and 50° C. (Scheme 16).

Scheme 16

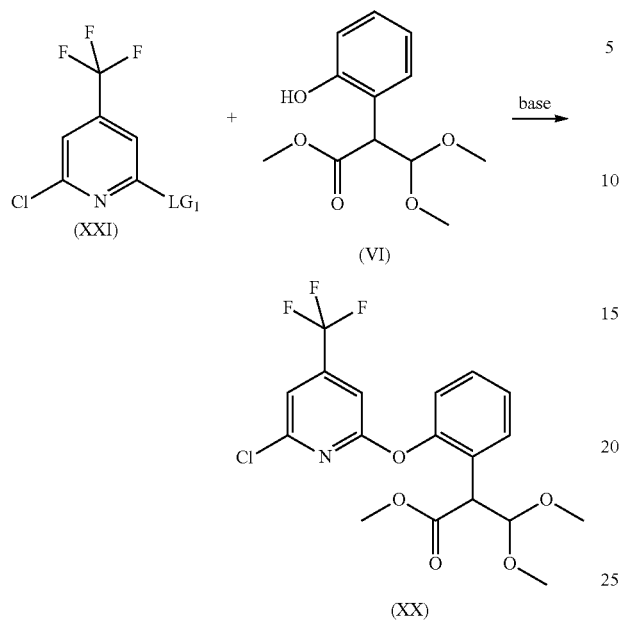

Compound XXIa with LG1=Cl is a known compound (Dow U.S. Pat. No. 3,705,170, 1972) and can be prepared by known procedures.

Alternatively compound of formula XVIII can be prepared by methylation of compound XXII. The methylation can be performed with methyliodide or dimethylsulfate, preferably dimethylsulfate, as methylation reagents in the presence of a base. The base can be a carbonate salt such as $Na_2CO_3$, $K_2CO_3$, $Cs_2CO_3$ more preferably $K_2CO_3$; an alkoxide base such as NaOMe or NaOtBu, a hydroxide base such as NaOH or KOH. The reaction can be carried out neat or in a solvent. The solvent can be MeOH, $H_2O$, EtOAc, toluene, benzene, pentane, hexane, heptane, acetone, THF, NMP DMF, dimethylacetamide, or DMSO. The reaction can be performed in the presence of a phase transfer catalyst, for example an ammonium salt, preferably tetrabutylammonium bromide. The reaction can be carried out between 0° C. and the boiling point of the used solvent, preferably between 20° C. and 80° C., most preferably at 20° C. and 40° C. (Scheme 17).

Scheme 17

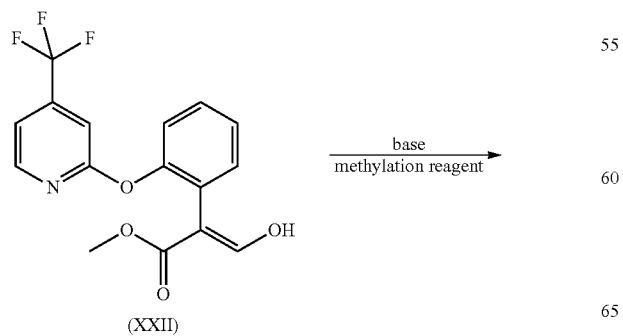

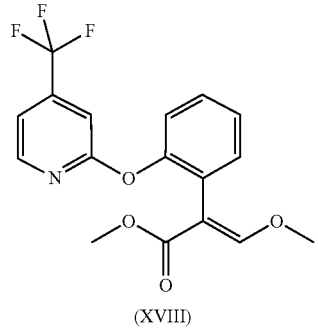

Compound XXII can be obtained by the reaction of phenylacetic acid derivative XXIII with methylformate in the presence of a Lewis acid, for example titantetrachloride as described in US 20100179320 or similar conditions. The solvent can be a halogenated organic solvent, for example dichloromethane or 1,2-dichloroethane (Scheme 18).

Scheme 18

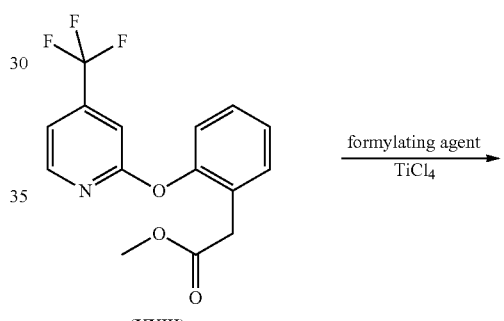

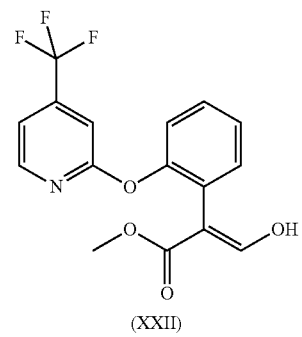

Alternatively compound XXII can be obtained by hydrolysis of enamine XXIV preferably in the presence of an acid, for example hydrochloric acid. The hydrolysis can be performed neat or in a solvent. There reaction is performed preferably in a solvent, for example an alcohol, for example methanol. There reaction is performed between −50° C. and 50° C., preferably between −20° C. and 30° C. (Scheme 19).

Scheme 19

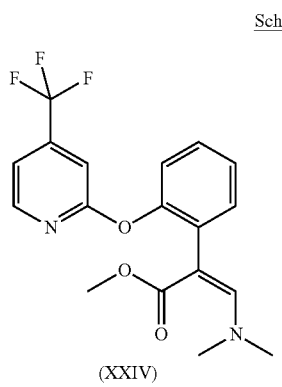

(XXIV)

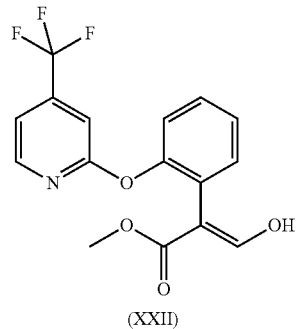

(XXII)

Enamine XXIV is prepared by reaction of phenylacetic acid derivative XXIII with DMF-DMA. The reaction can be carried out neat or in solvent, such as DMF or dimethylacetamide. There reaction is performed between 100° C. and the boiling point of the solvent, preferably between 140° C. and 160° C. (Scheme 20).

Scheme 20

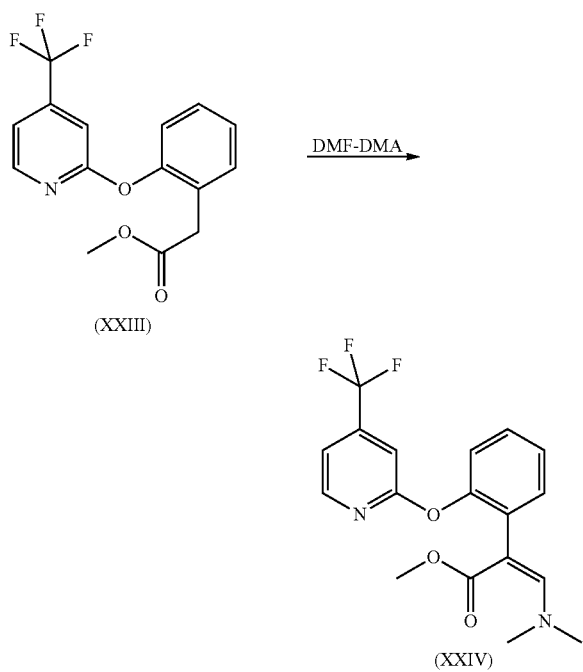

Phenylacetic acid derivative XXIII is obtained by esterification of acid XXV. The esterification can be performed in methanol in the presence of acid, for example catalytic amounts of methanesulfonic acid. The reaction is performed preferably under reflux. Alternatively phenylacetic acid derivative XXIII is obtained by reaction of acid XXV with a methylation reagent, such as dimethylsulfate in the presence of a base. The base can be an inorganic salt, preferably $Na_2CO_3$, $K_2CO_3$, $Cs_2CO_3$, NaOMe or NaH, NaOtBu, NaOH, and KOH; more preferably $K_2CO_3$. The reaction can be carried out neat or in a solvent. The solvent can be MeOH, EtOAc, toluene, benzene, pentane, hexane, heptane, acetone, THF, NMP DMF, dimethylacetamide, or DMSO. The reaction can be performed between 0° C. and 50° C., preferably between 15° C. and 30° C. (Scheme 21).

The reaction can also be carried out using an acid catalyst such as methanesulfonic acid, hydrogen chloride or $H_2SO_4$, more preferably methanesulfonic acid. The reaction is carried in the presence of at least one equivalent of MeOH. MeOH can be used either as a reagent or as a solvent. Other solvents can be used, such as toluene, benzene, pentane, hexane, heptane THF, NMP DMF, dimethylacetamide, or DMSO. The reaction can be performed between 25° C. and the boiling point of the solvent, more preferably between 50° C. and 100° C. (Scheme 21)

Scheme 21

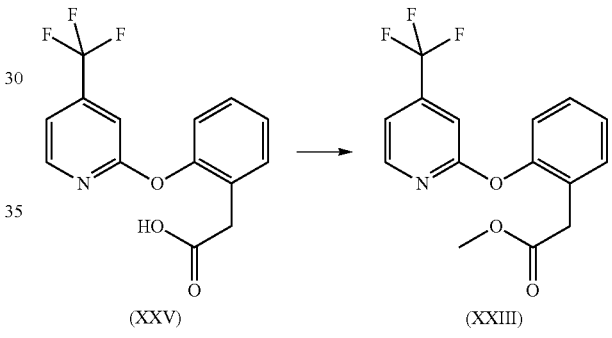

The acid XXV can be obtained by reaction of pyridine compound XXVI in which LG2 is a leaving group and 2-(2-hydroxyphenyl)acetic acid XXVII in the presence of a base. The leaving group LG2 is halogen, preferably chlorine or fluorine. The base can be an inorganic salt, preferably $Na_2CO_3$, $K_2CO_3$, $Cs_2CO_3$, NaOMe or NaH, NaOtBu, NaOH, and KOH; more preferably $K_2CO_3$. The reaction can be carried out neat or in a solvent. The solvent can be toluene, NMP, DMF, dimethylacetamide, or DMSO. The preferred solvents are DMF or dimethyl acetamide The reaction can be performed between 80° C. and the boiling point of the solvent, preferably between 140 and 180° C. (Scheme 22).

Scheme 22

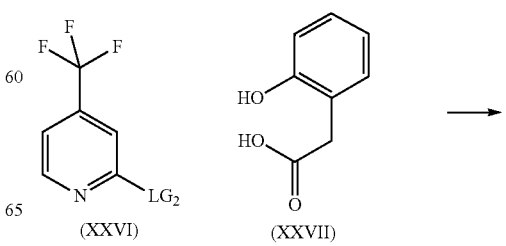

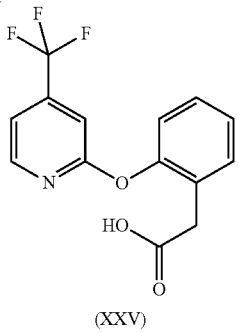

(XXV)

Compound XXVIa wherein LG2 is a chlorine is a known compound (Ishihara Sangyo Kaisha EP 42696, 1981) and can be prepared by known procedures.

Compound XXVIb wherein LG2 is a fluorine is a known compound (Dow U.S. Pat. No. 4,775,762, 1988) and can be prepared by known procedures.

2-(2-hydroxyphenyl)acetic acid XXVII is a known compound (Journal of the American Chemical Society (1948), 70, 1930) and can be prepared by known procedures.

The intermediates disclosed herein can be in the form of a geometric isomer, or salt, or a N-oxide thereof.

As well as the biological efficacy of the compound of the present invention against mosquitoes and resistant strains of such mosquitoes, other considerations for selecting a suitable compound could include its safety (such as its toxicity, persistence) to the environment, including to the users of a vector control product/method; its suitability for making a vector control product (whether indoor residual spray formulation, mosquito net, or another type), its suitability for adherence and availability on a surface over a period of time (in the event the product is an indoor residual spray), and also its suitability for incorporation into a polymer product (such as a net) so that the compound would be readily available to control mosquitoes on the surface of the net over a period of time and the nets can withstand multiple washings.

The compound of the first aspect has been found to be useful in control of mosquitoes.

Mosquito vector control is any method to limit or eradicate mosquito species which transmit disease pathogens. The most frequent types of mosquito vector control employ a variety of strategies.

Mosquito vector control focuses on utilizing preventative methods to control or eliminate mosquito populations. Common preventative measures are habitat control—removing or reducing areas where mosquitoes can easily breed can help limit population growth. For example, stagnant water removal, destruction of old tires and cans which serve as mosquito breeding environments and good management of stored water can reduce areas of excessive mosquito incidence.

reducing contact—limiting exposure to mosquitoes can reduce infection risks significantly. For example, bed nets, window screens on homes, or protective clothing can help reduce the likelihood contact with mosquitoes. To be effective this requires education and promotion of methods among the population to raise the awareness of mosquito threats.

chemical control—insecticides, larvicides, and repellents can be used to control mosquitoes. For example, larvicides can be used in mosquito breeding zones; insecticides can be applied to house walls or bed nets, and use of personal repellents can reduce incidence of mosquito bites and thus infection. The use of pesticides for mosquito vector control is promoted by the World Health Organization (WHO) and has proven to be highly effective.

biological control—the use of natural mosquito vector predators, such as bacterial toxins or botanical compounds, can help control mosquito populations. Using fish that eat mosquito larvae, has been demonstrated to have some success.

population control through the release of sterilized, or genetically modified, male mosquitoes has also been shown to control mosquito vector populations and reduce infection risks.

A number of considerations is taken into account when determining a compound would be suitable for use in a particular mosquito vector control strategy, such as favourable safety profile, biological performance and affordability—the compound of the first aspect demonstrates an attractive profile.

In one embodiment—the compound of the first aspect in accordance with the methods and other aspects of the present invention are useful in controlling mosquitoes, in particular mosquitoes selected from the genus *Anopheles*, *Culex* and *Aedes*. Examples include *Aedes aegypti*, *Aedes albopictus*, *Aedes japonicas*, *Aedes vexans*, *Coquillettidia perturbans*, *Culex molestus*, *Culex pallens*, *Culex pipiens*, *Culex quinquefasciatus*, *Culex restuans*, *Culex tarsalis*, *Anopheles albimanus*, *Anopheles albitarsis*, *Anopheles annularis*, *Anopheles aquasalis*, *Anopheles arabiensis*, *Anopheles aconitus*, *Anopheles atroparvus*, *Anopheles balabacensis*, *Anopheles culicifacies*, *Anopheles coluzzii*, *Anopheles darlingi*, *Anopheles dirus*, *Anopheles farauti*, *Anopheles flavirostris*, *Anopheles fluviatilis*, *Anopheles freeborni*, *Anopheles funestus*, *Anopheles gambiae* s.l., *Anopheles koliensis*, *Anopheles labranchiae*, *Anopheles lesteri*, *Anopheles leucosphyrus*, *Anopheles maculatus*, *Anopheles marajoara*, *Anopheles melas*, *Anopheles merus*, *Anopheles messeae*, *Anopheles minimus*, *Anopheles moucheti*, *Anopheles nili*, *Anopheles nuneztovari*, *Anopheles plumbeus*, *Anopheles pseudopunctipennis*, *Anopheles punctipennis*, *Anopheles punctulatus*, *Anopheles quadrimaculatus*, *Anopheles sacharovi*, *Anopheles sergentii*, *Anopheles sinensis*, *Anopheles stephensi*, *Anopheles subpictus*, *Anopheles sundaicus*, *Anopheles superpictus*, and *Mansonia titillans*, *Ochlerotatus stimulans*, *Ochlerotatus japonicas* (each of which is an example of a mosquito capable of carrying or vectoring a pathogenic disease).

By control is meant that the compound of the first aspect useful in the methods and other aspects of the invention is employed in a manner that kills or repels the mosquito such that biting does not occur or in a manner that decreases mosquito populations such that biting does not occur as frequently.

In an especially preferred embodiment, the compound of the first is useful in controlling a mosquito selected from the genus *Anopheles*, *Culex* and *Aedes*, in particular *Aedes aegypti*, *Aedes albopictus*, *Aedes japonicas*, *Aedes vexans*, *Culex molestus*, *Culex pallens*, *Culex pipiens*, *Culex quinquefasciatus*, *Culex restuans*, *Culex tarsalis*, *Anopheles albimanus*, *Anopheles arabiensis*, *Anopheles coluzzii*, *Anopheles darlingi*, *Anopheles dirus*, *Anopheles funestus*, *Anopheles gambiae* s.l., *Anopheles melas*, *Anopheles minimus*, *Anopheles sinensis*, *Anopheles stephensi*, *Mansonia titillans*.

In an embodiment, the compound of the first aspect is useful in the methods and other aspects of the invention to control adult mosquitoes.

In another embodiment the compound of the first aspect is especially useful in controlling one or more of the following mosquitoes: *Aedes aegypti, Anopheles funestus, Anopheles gambiae* s.I., *Anopheles stephensi, Anopheles arabiensis, Aedes albopictus* and *Anopheles coluzzii*.

Insecticide resistant mosquito species have also been detected and accordingly in an embodiment, the compound of the first aspect useful in the methods and other aspects of the invention is suitable for controlling insecticide-resistant mosquitoes, such as pyrethroid and/or carbamate-resistant mosquitoes.

Pyrethroids are the only insecticides that have obtained WHO recommendation against malaria vectors on both Indoor Residuals Sprays (IRS) and Long Lasting Insecticidal Mosquito Nets (LLINs), in the form of alpha-cypermethrin, bifenthrin, cyfluthrin, permethrin, deltamethrin, lambda-cyhalothrin and etofenprox. It has been the chemical class of choice in agriculture and public health applications over the last several decades because of its relatively low toxicity to humans, rapid knock-down effect, relative longevity (duration of 3-6 months when used as IRS), and low cost. However, massive use of pyrethroids in agricultural applications and for vector control led to the development of resistance in major malaria and dengue vectors. Strong resistance has, e.g., been reported for the pyrethroid deltamethrin (and permethrin) for the *Anopheles gambiae* Tiassalé (from southern Cote d'Ivoire) strain (Constant V. A. Edi et al., Emerging Infectious Diseases; Vol. 18, No. 9, September 2012). Pyrethroid resistance was also reported for permethrin, deltamethrin and lambda-cyhalothrin for the *Aedes aegypti* Cayman Island strain (Angela F. Harris et al., Am. J. Trop. Med. Hyg., 83(2), 2010) and alpha-cypermethrin, permethrin and lambda-cyhalothrin for certain *Anopheles* strains (Win Van Bortel, Malaria Journal, 2008, 7:102).

In another embodiment of the invention, the compound of the first aspect can be suitable for use against insecticide-resistant mosquitoes that are selected from Cote d'Ivoire: *Anopheles gambiae* "Tiassale"; Tanzania: *Anopheles arabiensis* "Lupiro"; Cameroon: *Anopheles funestus* "Mibelong"; and Benin: *Anopheles gambiae* "Cove".

In another embodiment of the invention, the compound of the first aspect can be suitable for use against insecticide-resistant mosquitoes that are selected from *Anopheles gambiae* RSPH, *Anopheles gambiae* Tiassalé, *Anopheles gambiae* Akron, *Anopheles gambiae* Kisumi Rdl, *Anopheles arabiensis* NDjamina, *Anopheles coluzzii* VK7, *Anopheles funestus* FUMOZ, *Aedes aegypti* Grand Cayman and *Culex quinquefasciatus* strain POO.

*Anopheles gambiae*, strain RSPH is a multi-resistant mosquito (target-site and metabolic-resistance) that is described in the reagent catalogue of the Malaria Research and Reference Reagent Resource Center (www.MR4.org; MR4-number: MRA-334).

*Anopheles gambiae*, strain Tiassalé is a multi-resistant mosquito (target and metabolic-resistant strain) which shows cross-resistance between carbamates, organophosphates and pyrethroids and is described in Constant V. A. Edi et al., Emerging Infectious Diseases; Vol. 18, No. 9, September 2012 and Ludovic P Ahoua Alou et al., Malaria Journal 9: 167, 2010).

*Anopheles gambiae*, strain Akron is a multi-resistant mosquito (target and metabolic-resistant strain) and is described in Djouaka F Rousseau et al., BMC Genomics, 9:538; 2008.

*Anopheles coluzzii*, strain VK7 is a mosquito population with target site and metabolic resistance mechanisms, and is described in Toe et al, BMC Genomics 2015, 16:146.

*Anopheles funestus*, strain FUMOZ is a metabolic-resistant strain and is described in Hunt et al., Med Vet Entomol. 2005 September; 19(3):271-5). In this article it has been reported that *Anopheles funestus*—as one of the major malaria vector mosquitoes in Africa—showed resistance to pyrethroids and carbamate insecticides in South Africa.

*Anopheles gambiae*, strain Kisumi Rdl, a dieldrin resistant strain from Kenya.

*Anopheles arabiensis*, strain NDjamina, a pyrethroid resistant from Chad.

*Aedes aegypti*, strain Grand Cayman is a target-resistant mosquito and is described in Angela F. Harris, Am. J. Tro. Med. Hyg. 83(2), 2010.

*Culex quinquefasciatus* (metabolic-resistant to DDT strain P00); received from Texchem, Penang, Malaysia.

Vector control management methods or products are means to control a vector, such as a mosquito. Examples of such methods include use of compositions, products, and treated articles of the present invention, such as a substrate or non-living material incorporating (e.g., coated or impregnated with) the compound of the first aspect, spray products (e.g., indoor sprays) comprising the compound of the first aspect, paint compositions comprising the compound of the first aspect, and products or treated articles comprising the compound of the first aspect.

Examples of vector control management methods & products of the invention, such as methods for controlling mosquito bites or decreasing relevant mosquito populations, include the use of such compositions, products, treated articles and substrates of the invention at a locus of potential or known interaction between the mosquito vector and an animal, including a human, that is susceptible to a pathogenic disease infection transmitted by such vector. Suitable vector control management methods & products within the scope of the present invention also include identifying mosquito breeding sites and positioning compositions, products, treated articles and substrates of the invention at such sites.

Examples of a substrate or non-living material of the invention are self-supporting film/sheet (e.g., screens), threads, fibres, yarns, pellets, weaves (or textiles (e.g., for clothing)), nets, tents, and curtains incorporating (e.g., coated or impregnated with) the compound of the first aspect, which can be used to protect against mosquito bites. In particular, it is well known that humans can be protected in their sleep from mosquito stings by insecticidally coated sleeping nets. Coated or impregnated weaves of the invention can also be used as curtains in front of windows, doors open eaves, or ventilation openings, in order to control mosquito entering dwellings.

The use of a compound in a substrate of the present invention (e.g., nets and weaves) achieves at least one of the following objects:
good insecticidal effect
fast-acting insecticidal efficacy
long-lasting insecticidal efficacy
uniform release of active ingredient
long durability (including resisting multiple washings over an extended period)
simple production
safe to the user The nets and weaves (or textiles) of the invention that incorporate (e.g., are coated or impregnated with) the compound of the first aspect are made up of a variety of natural and synthetic fibres, also as textile blends in woven or non-woven form, as knit goods or fibres. Natural fibres are, for example, raffia, jute, flax, sisal, hessian, wool, silk or hemp. Synthetic fibres may be made of polyamides, polyesters, polyacrylonitriles, polyolefines, for example polypropylene or polyethylene, Teflon, and mixtures of fibres, for example mixtures of synthetic and natural fibres. Polyamides, polyolefins and polyesters are preferred as fibre material. Polyester, such a polyethylene terephthalate, polyethylene and polypropylene are especially preferred. Most preferred are nettings made from polyethylene and/or polypropylene.

The art discloses methods suitable for incorporating (by way of coating) a compound onto nets and weaves (see for example, WO2003/034823, WO 2008/122287, WO 01/37662, US2009036547, WO 2007/036710), from dipping or submerging them into a formulation of the insecticide or by spraying the formulation onto their surfaces. After treating the nets and weaves of the invention, they may be dried simply at ambient temperatures (see also below for more background). Such methods are also suitable for incorporating (by way of coating) the compound of the first aspect.

Also disclosed in the art are methods suitable for incorporating (by way of impregnating) a pesticide compound within the net or weave by making polymer material in the presence of the compound, which is then extruded into fibres, threads or yarns, for making the nets and weaves (see for example, WO08004711, WO2009/121580, WO2011/128380, WO2011/141260, WO2010/118743). Such nets and weaves having available at the surface of the net and weave an effective amount of the compound so as to control mosquito bites. Generally the compound is mixed with the molten polymer. Such methods are also suitable for incorporating (by way of impregnating) the compound of the first aspect.

The term "incorporating" or "incorporated" in context of the compound of the invention, additives and other insecticides is meant that the substrate or non-living material comprises or contains the respectively defined compound, additive and/or insecticide, such as by coating or impregnation.

Preferably the substrate of the present invention is a net, which net is preferably a long lasting net, incorporated with the compound of the first aspect by way of coating the net with a composition comprising the compound of the first aspect, or by way of making a polymeric material in the presence of the compound of the first aspect and then processing the resultant polymeric material into an inventive net.

In accordance with the invention, when the compound of the first aspect is used within the polymer, then during use of the resulting net or weave made from the polymer, the compound of the first aspect is released to the surface of the net to control against mosquito bites—such control is sustained at adequate level and for adequate amount of time.

Examples of suitable polymers are polyamides, polyesters, polyacrylonitriles, polyolefines, such as polyethylene compositions that can be made from different polyethylene polymers; these may be LDPE, LLDPE, MDPE and HDPE. LLDPE (Linear low-density polyethylene) is a substantially linear polymer (polyethylene), with significant numbers of short branches, commonly made by copolymerization of ethylene with longer-chain olefins. MDPE is medium-density polyethylene is a substantially linear polymer of polyethylene with shorter chain length than HDPE. HDPE (High-Density PolyEthylene) or PolyEthylene High-Density (PEHD) is a polyethylene thermoplast. HDPE has little branching, giving it stronger intermolecular forces and tensile strength than lower-density polyethylene. It is also harder and more opaque and can withstand somewhat higher temperatures (120 degrees Centigrade/248 degrees Fahrenheit for short periods, 110 degrees Centigrade/230 degrees Fahrenheit continuously). HDPE yarns are stronger than LDPE mixed polyethylene yarns. LLDPE differs structurally from conventional low-density polyethylene (LDPE) because of the absence of long chain branching. These polyethylene compositions (HDPE, LDPE, LLDPE and mixture thereof) are generally used for preparing yarns and polyethylene based textile products. Methods for incorporating an insecticide compound into the polymer without weakening its resulting properties are known in the art, such as using mixtures of HDPE and LDPE. Such methods can also be used to incorporate the compound of the first aspect into a polymer.

Examples of spray products of the present invention are indoor residual sprays or space sprays comprising the compound of the first aspect. Indoor Residual Spraying (IRS) is the technique of applying a residual deposit of an insecticide onto indoor surfaces where vectors rest, such as on walls and ceilings. The primary goal of indoor residual spraying is to reduce the lifespan of the mosquito vectors and thereby reduce or interrupt disease transmission. The secondary impact is to reduce the density of mosquitoes within the treatment area. IRS is a recognised, proven and cost-effective intervention method for the control of malaria and it is also used in the management of Leishmaniasis disease. Many malaria mosquito vectors are endophilic, resting inside houses after taking a blood meal. These mosquitoes are particularly susceptible to control through indoor residual spraying (IRS) comprising the compound of the first aspect. As its name implies, IRS involves coating the walls and other surfaces of a house with a residual insecticide. For several months, the compound of the first aspect will kill mosquitoes that come in contact with these surfaces. IRS does not directly prevent people from being bitten by mosquitoes. Rather, it usually kills mosquitoes after they have fed, if they come to rest on the sprayed surface. IRS thus prevents transmission of infection to other persons. To be effective, IRS must be applied to a very high proportion of households in an area (usually greater than 70 percent). Although the community plays a passive role in IRS programs, cooperation with an IRS effort is a key to its success. Community participation for IRS often consists of cooperating with the spray teams by removing food and covering surfaces prior to spraying and refraining from covering the treated surfaces with new paint or plaster. However, community or individual householder opposition to IRS due to the smell, mess, possible chemical exposure, or sheer bother has become a serious problem in some areas. Therefore, sprays in accordance with the invention having good residual efficacy and acceptable odour are particularly suited as a component of vector control management.

In contrast to IRS, which requires that the active compound of the first aspect is bound to surfaces of dwellings, such as walls, ceiling, space spray products of the invention rely on the production of a large number of small insecticidal droplets intended to be distributed through a volume of air over a given period of time. When these droplets impact on a target mosquito, they deliver a lethal dose of the compound of the first aspect. The space-spray include thermal fogging (whereby a dense cloud of insecticide droplets is produced giving the appearance of a thick fog) and Ultra Low Volume (ULV), whereby droplets are produced by a cold, mechanical aerosol-generating machine.

Since large areas can be treated at any one time this method is a very effective way to rapidly reduce the population of flying mosquitoes in a specific area. Since there is very limited residual activity from the application it must be repeated at intervals of 5-7 days in order to be fully effective. This method can be particularly effective in epidemic situations where rapid reduction in mosquito numbers is required. As such, it can be used in urban dengue control campaigns.

Effective space-spraying is generally dependent upon the following specific principles:
  Target insects are usually flying through the spray cloud (or are sometimes impacted whilst resting on exposed surfaces). The efficiency of contact between the spray droplets and target insects is therefore crucial. This is achieved by ensuring that spray droplets remain airborne for the optimum period of time and that they contain the right dose of insecticide. These two issues are largely addressed through optimizing the droplet size.
  If droplets are too big they drop to the ground too quickly and don't penetrate vegetation or other obstacles encountered during application (limiting the effective area of application). If one of these big droplets impacts an individual insect then it is also 'overkill' since a high dose will be delivered per individual insect.
  If droplets are too small then they may either not deposit on a target insect (no impaction) due to aerodynamics or they can be carried upwards into the atmosphere by convection currents.
  The optimum size of droplets for space-spray application are droplets with a Volume Median Diameter (VMD) of 10-25 microns.

The compositions of the present invention may be made available in a spray product as an aerosol-based application, including aerosolized foam applications. Pressurised cans are the typical vehicle for the formation of aerosols. An aerosol propellant that is compatible with the compound of the first aspect is used. Preferably, a liquefied-gas type propellant is used. Suitable propellants include compressed air, carbon dioxide, butane and nitrogen. The concentration of the propellant in the composition is from about 5 percent to about 40 percent by weight of the composition, preferably from about 15 percent to about 30 percent by weight of the composition.

In one embodiment, the formulation of the invention comprising the compound of the first aspect can also include one or more foaming agents. Foaming agents that can be used include sodium laureth sulphate, cocamide DEA, and cocamidopropyl betaine. Preferably, the sodium laureth sulphate, cocamide DEA and cocamidopropyl are used in combination. The concentration of the foaming agent(s) in the composition is from about 10 percent to about 25 percent by weight, more preferably 15 percent to 20 percent by weight of the composition.

When the compound of the first aspect formulation is used in an aerosol application not containing foaming agents), the composition of the present invention can be used without the need for mixing directly prior to use. However, aerosol formulations containing the foaming agents do require mixing (i.e. shaking) immediately prior to use. In addition, if the formulations containing foaming agents are used for an extended time, they may require additional mixing at periodic intervals during use.

A dwelling area may also be treated with composition comprising the compound of the first aspect by using a burning formulation, such as a candle, a smoke coil or a piece of incense containing the composition. For example, composition may be comprised in household products such as "heated" air fresheners in which insecticidal compositions are released upon heating, for example, electrically, or by burning.

The compositions of the present invention containing the compound of the first aspect may be made available in a spray product as an aerosol, a mosquito coil, and/or a vaporiser or fogger.

The concentration of the compound of the first aspect in the polymeric material, fibre, yarn, weave, net, or substrate, each of the invention, can be varied within a relatively wide concentration range from, for example 0.05 to 15 percent by weight, preferably 0.2 to 10 percent by weight, more preferably 0.4 to 8 percent by weight, especially 0.5 to 5, such as 1 to 3, percent by weight.

The percentages mentioned above are based on dry weight of the net or substrate or non-living material.

Similarly, the concentration of the compound of the invention in the composition (whether for treating surfaces or for coating a fibre, yarn, net, weave) can be varied within a relatively wide concentration range from, for example 0.1 to 70 percent by weight, such as 0.5 to 50 percent by weight, preferably 1 to 40 percent by weight, more preferably 5 to 30 percent by weight, especially 10 to 20 percent by weight.

The concentration shall be chosen according to the field of application such that the requirements concerning insecticidal efficacy, durability and toxicity are met. Adapting the properties of the material can also be accomplished and so custom-tailored textile fabrics are obtainable in this way.

The compound of the first aspect when used in the IRS methods of the invention is present on a surface of a dwelling at a coverage of from 0.01 to 2 grams of Al per m2, preferably from 0.05 to 1 grams of Al per m2, especially from 0.1 to 0.7 grams of Al per m2.

Accordingly an effective amount of the compound of the first aspect can depend on how it is being used, the mosquito against which control is most desired and the environment it is being used in. Therefore, an effective amount of the compound of the first aspect is sufficient that control of a mosquito is achieved; in case of:
  use as a IRS formulation, the effective amount is such that coverage of the Al on the surface is from 0.01 to 2 grams of Al per m2, preferably from 0.05 to 1 grams of Al per m2, especially from 0.1 to 0.7 grams of Al per m2;
  use incorporated within a net or substrate, the effective amount is 0.05 to 15 percent by weight, preferably 0.2 to 10 percent by weight, more preferably 0.4 to 8 percent by weight, especially 0.5 to 5, such as 1 to 3, percent by weight.

Generally the compound of the first aspect when used in certain products of the invention is continuously distributed in a thread, yarn, net or weave, but can also be partially or discontinuously distributed in a thread, yarn, net or weave. For example, a net may contain certain parts which are coated or which is made-up of impregnated fibre, and certain other parts which are not; alternatively some of the fibres making up the net is impregnated, or is coated, with the compound of the invention, and some of the other fibres not or these other fibres are impregnated, or are coated, with another insecticide compound (see below).

Nets of the invention impregnated, or coated, with the compound of the first aspect can satisfy the criteria of the WHOPES directive (see "Guidelines for laboratory and field testing of long-lasting insecticidal mosquito nets", 2005, http://www.who.int/whopes/guidelines/en/) for insecticide-containing long-lasting mosquito nets up to 20 washes only, which means that such nets should not lose their biological activity after just 20 wash cycles or so.

In an embodiment, a net of the invention impregnated, or coated, with the compound of the first aspect can have biological activity in accordance with WHOPES guidelines of a knockdown after 60 minutes of between 95 percent and 100 percent or a mortality after 24 hours of between 80 percent and 100 percent after at least 20, such as 25, preferably at least 30 and even more preferably at least 35 washes.

The "WHOPES directive" is to be understood as meaning the directive "Guidelines for laboratory and field testing of long-lasting insecticidal mosquito nets", 2005). This directive is retrievable at the following interact address: http://www.who.int/whopes/guidelines/en/.

When a net is "impregnated with" the compound of the first aspect to prepare a net of the present invention, the fibres making up the net are made by melting a polymer, the compound of the first aspect and optionally other compounds, such as other insecticides, additives, stabilisers. When a net is impregnated with the compound of the first aspect, then the net of the invention contains synthetic fibres; whereas, a net of the invention coated with the compound of the first aspect contains synthetic fibres and/or natural fibres.

The polymeric materials useful in the compositions of the invention incorporating the compound of the first aspect can be produced by mixing the compound of the first aspect with the polymer in the liquid phase, and optionally other additives (such as binders and/or synergists), and other insecticidal compounds.

Methods of making suitable polymeric materials and then processing it are described in the art—see for example, WO09121580, WO2011/141260.

For example, nets based on an insecticide-containing polymeric material are produced by the following steps:
a) melting the polymer to be used and one or more insecticidally active ingredients together or separately at temperatures between 120 and 250 degrees centigrade,
b) forming the melt of step a) into spun threads and cooling,
c) optionally leading the spun threads formed in step b) through a drawing system and drawing and then optionally setting out the threads,
d) knitting the spun threads to form a net,
e) subjecting the net to a heat-setting operation wherein the temperature for the heat-setting operation is chosen to be 20 degrees centigrade below the melting temperature of the polymer to be used.

The heat setting in step e) of the production of the nets is preceded by a washing step. Water and a detergent is preferably used for this. The heat setting is preferably carried out in a dry atmosphere.

Although the manufacture of the nets incorporated with a compound can occur in a single location, it is also envisaged that the different steps can take place in different locations. So a composition comprising the compound of the first aspect may be made which can then be processed into a polymer. Accordingly, the present invention also provides a composition comprising the compound of the first aspect in a concentrated form, which composition may also contain additives (such as binders and/or synergists), and other insecticidal compound(s) (which composition had been prepared explicitly for making a polymer material impregnated with the compound of the first aspect (such a composition is often referred to as a "masterbatch")). The amount of the compound of the first aspect in the masterbatch would depend on the circumstances, but in general can be 10 to 95 percent by weight, such as 20 to 90 percent by weight, preferably 30 to 85 percent by weight, more preferably 35 to 80 percent by weight, especially 40 to 75 percent by weight.

Also made available in the present invention are compositions or formulations for coating walls, floors and ceilings inside of buildings and for coating a substrate or non-living material, which comprise the compound of the first aspect. The inventive compositions can be prepared using known techniques for the purpose in mind, which could contain a binder to facilitate the binding of the compound to the surface or other substrate. Agents useful for binding are known in the art and tend to be polymeric in form. The type of binder suitable for composition to be applied to a wall surface having particular porosities, binding characteristics would be different to a fibre, yarn, weave or net—a skilled person, based on known teachings, would select a suitable binder.

Typical binders are poly vinyl alcohol, modified starch, poly vinyl acrylate, polyacrylic, polyvinyl acetate co polymer, polyurethane, and modified vegetable oils. Suitable binders can include latex dispersions derived from a wide variety of polymers and co-polymers and combinations thereof. Suitable latexes for use as binders in the inventive compositions comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, as well as post-dispersed suspensions of silicones or polyurethanes. Also suitable may be a polytetrafluoroethylene (PTFE) polymer for binding the active ingredient to other surfaces.

The formulation according to the present invention comprises the compound of the first aspect (or a pesticide (A), and a carrier, such as water (C), and optionally a polymeric binder (B) and further components (D).

The polymeric binder binds the compound of the first aspect to the surface of the non-living material and ensures a long-term effect. Using the binder reduces the elimination of the pesticide (A) out of the non-living material due to environmental effects such as rain or due to human impact on the non-living material such as washing and/or cleaning it. The further components can be an additional insecticide compound, a synergist, a UV stabiliser.

The inventive compositions can be in a number of different forms or formulation types, such as suspensions, capsules suspensions, and a person skilled in the art can prepare the relevant composition based on the properties of the compound of the first aspect, its uses and also application type.

For example, the compound of the first aspect used in the methods and other aspects of the present invention may be encapsulated in the formulation. A encapsulated compound can provide improved wash-fastness and also longer period of activity. The formulation can be organic based or aqueous based, preferably aqueous based.

A microencapsulated compound suitable for use in the compositions and methods according to the invention are prepared by any suitable technique known in the art. For example, various processes for microencapsulating material have been previously developed. These processes can be divided into three categories-physical methods, phase separation and interfacial reaction. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, microcapsules are formed by emulsifying or dispersing the core material in an immiscible continuous phase and then an interfacial polymerization reaction is caused to take place at the surface of the core particles. The concentration of the compound of the first aspect present in the microcapsules can vary from 0.1 to 60% by weight of the microcapsule.

The formulation according to the invention may be formed by mixing all ingredients together with water optionally using suitable mixing and/or dispersing aggregates. In general, the formulation is formed at a temperature of from 10 to 70 degrees centigrade, preferably 15 to 50 degrees centigrade, more preferably 20 to 40 degrees centigrade It is possible to use a pesticide (A), solid polymer (B) and optionally additional additives (D) and to disperse them in the aqueous component (C)

If a binder is present in a composition of the present invention, it is preferred to use dispersions of the polymeric binder (B) in water as well as aqueous formulations of the pesticide (A) in water which have been separately prepared before. Such separate formulations may contain additional additives for stabilizing (A) and/or (B) in the respective formulations and are commercially available. In a second process step, such raw formulations and optionally additional water (component (C)) are added.

Also combinations are possible, i.e. using a pre-formed dispersion of (A) and/or (B) and mixing it with solid (A) and/or (B).

A dispersion of the polymeric binder (B) may be a pre-manufactured dispersion already made by a chemicals manufacturer.

However, it is also within the scope of the present invention to use "hand-made" dispersions, i.e. dispersions made in small-scale by an end-user. Such dispersions may be made by providing a mixture of about 20 percent of the binder (B) in water, heating the mixture to temperature of 90 to 100 degrees centigrade and intensively stirring the mixture for several hours.

It is possible to manufacture the formulation as a final product so that it can be readily used by the end-user for the process according to the present invention.

However, it is of course also possible to manufacture a concentrate, which may be diluted by the end-user with additional water (C) to the desired concentration for use.

In an embodiment, a composition suitable for IRS application or a coating formulation containing the compound of the first aspect contains the active ingredient and a carrier, such as water, and may also one or more co-formulants selected from a dispersant, a wetter, an anti-freeze, a thickener, a preservative, an emulsifier and a binder or sticker.

The compound of the first aspect is generally milled to a desired particle size, such as the particle size distribution d(0.5) is generally from 3 to 20, preferably 5 to 15, especially 7 to 12, μm.

Furthermore, it may be possible to ship the formulation to the end-user as a kit comprising at least a first component comprising the compound of the first aspect (A); and a second component comprising at least one polymeric binder (B).

Further additives (D) may be a third separate component of the kit, or may be already mixed with components (A) and/or (B).

The end-user may prepare the formulation for use by just adding water (C) to the components of the kit and mixing.

The components of the kit may also be formulations in water. Of course it is possible to combine an aqueous formulation of one of the components with a dry formulation of the other component(s).

As an example, the kit can comprise one formulation of the compound of the first aspect (A) and optionally water (C); and a second, separate formulation of at least one polymeric binder (B), water as component (C) and optionally components (D).

Accordingly, in a further aspect the present invention provides a kit for treating a fibre, yarn, net and weave by coating wash resistant insecticidal properties thereto comprising: a first sachet comprising a pre-measured amount of the compound of the first aspect, and a second sachet comprising a pre-measured amount of at least one polymeric binder. The resulting treated fibre, yarn, net and weave has imparted thereto the insecticidal properties needed for vector control, such as to control vector-carrying mosquitoes.

The concentrations of the components (A), (B), (C) and optionally (D) will be selected by the skilled artisan depending of the technique to be used for coating/treating.

In general, the amount of pesticide (A) may be up to 50, preferably 5 to 50, such as 10 to 40, especially 15 to 30, percent by weight, based on weight of the composition.

The amount of polymeric binder (B) may be in the range of 0.01 to 30, preferably 0.5 to 15, more preferably 1 to 10, especially 1 to 5, percent by weight, based on weight of the composition.

If present, in general the amount of additional components (D) is from 0.1 to 20, preferably 0.5 to 15, percent by weight, based on weight of the composition. If present, suitable amounts of pigments and/or dyestuffs are in general 0.01 to 5, preferably 0.1 to 3, more preferably 0.2 to 2, percent by weight, based on weight of the composition.

A typical formulation ready for use comprises 0.1 to 40, preferably 1 to 30, percent of components (A), (B), and optionally (D), the residual amount being water (C).

A typical concentration of a concentrate to be diluted by the end-user may comprise 5 to 70, preferably 10 to 60, percent of components (A), (B), and optionally (D), the residual amount being water (C).

The formulation of the present invention may be applied to polymeric material before their formation into the required products, e.g., while still a yarn or in sheet form, or after formation of the relevant products.

For the case of nets and/or weaves, a process for coating nets and/or weaves at least comprising the following steps:

a) treating the nets and/or weaves with the aqueous formulation according to the invention by any of the procedural steps selected from the group of
  (a1) passing the material through the formulation; or
  (a2) contacting the material with a roller that is partly or fully dipped into the formulation and drawing the formulation to the side of the material in contact with the roller, or
  (a3) submerging the material into the formulation; or
  (a4) spraying the formulation onto the material; or
  (a5) brushing the formulation onto or into the material; or
  (a6) applying the formulation as a foam; or
  (a7) coating the formulation onto material.
b) optionally removing surplus formulation by squeezing the material between rollers or by means of a doctor blade; and
c) drying the material.

In case the raw materials containing residues of preceding production processes, e.g., sizes, spin finishes, other auxiliaries and/or impurities, it may be beneficial to perform a washing step before the coating.

Specifically, the following details are important for the steps a), b), and c).

Step a1)

The formulation is applied by passing the material through the aqueous formulation. Said step is known by a person skilled in the art as padding. In a preferred embodiment the material is completely submerged in the aqueous formulation either in a trough containing the liquor or the material is passed through the formulation which is held between two horizontally oriented rollers. In accordance with the invention, the material may either be passed through the formulation or the formulation may be passed through the material. The amount of uptake of the formulation will be influenced by the stability of concentrated baths, the need for level distribution, the density of material and the wish to save energy costs for drying and curing steps. Usual liquor-uptakes may be 40 to 150 percent on the weight of material. A person skilled in the art is familiar with determining the optimum value. Step a1) is preferred for coating open-width material which is later tailored into nets.

For small-scale production or re-coating of non-treated nets, use of a simple hand-held roller may be sufficient.

Step a2)

It is further possible to apply the aqueous formulation on the material by a roller that is partly dipped into the dispersion thus applying the dispersion to the side of the material in contact with the roller (kiss-rolling). By this method it is possible to coat only one side of the material which is advantageous if, e.g., direct contact of the human skin with insecticide-treated material is to be avoided.

Coating of the material in step a1), a2) or a3) is typically carried out at temperatures from 10 to 70 degrees centigrade, preferably 15 to 50 degrees centigrade, more preferably 20 to 40 degrees centigrade Step a4)

The spray may be applied in continuous processes or in batch-wise processes in suitable textile machines equipped with a spraying device, e.g., in open-pocket garment washer/extractors. Such equipment is especially suitable for impregnating ready-made nets.

Step a6)

A foam comprises less water than the dispersion mentioned above. The drying process may therefore be very short. The treatment may be performed by injecting gas or blends of gas (e.g., air) into it. The addition of surfactants, preferably with film-forming properties, may be required. Suitable surfactants and the required technical equipment are known to persons skilled in the art.

Step a7)

A coating process may preferably carried out in a doctor-blade process. The process conditions are known to a person skilled in the art.

Step b)

The surplus emulsion is usually removed by squeezing the material, preferably by passing the material through rollers as known in the art thus achieving a defined liquor uptake. The squeezed-off liquor may be re-used. Alternatively, the surplus aqueous emulsion or aqueous dispersion may be removed by centrifuging or vacuum suction.

Step c)

Drying may be performed at ambient temperatures. In particular, such a passive drying may be carried out in hot-dry climate. Of course, the drying process may be accelerated applying elevated temperatures. An active drying process would normally be performed during high scale processing. The drying is in general carried out temperatures below 200 degrees centigrade. Preferred temperatures are from 30 to 170 degrees centigrade, more preferably at room temperature. The temperature choice is determined by the thermal stability of the insecticide in the formulation and the thermal stability of the non-living material impregnated.

For the method according to the invention aqueous formulation comprising at least one pigment and/or at least one dyestuff may be used so that the material is not only coated with the compound of the first aspect but in addition also coloured at the same time.

In a further aspect, the present invention provides a method for treating a fibre, yarn, net and weave by coating wash resistant insecticidal properties thereto comprising (i) preparing a treatment composition, which comprises the compound of the first aspect, (ii) treating said fibre, yarn, net and weave and (iii) drying the resulting treated a fibre, yarn, net and weave.

The polymeric binder (B) can be dispersed in an aqueous formulation and comprises one or more fluorinated acrylic copolymers useful in the water and oil resistant formulations includes copolymer prepared by the polymerization of a perfluoroalkyl acrylate monomer and a comonomer, especially an acrylate monomer. The binder may also be fluorocarbon resins (as described in WO 2006/128870.

Only water is used as solvent for the formulation. However, trace amounts of organic solvents miscible with water may be present. Examples of solvents comprise water-miscible alcohols, e.g., monoalcohols such as methanol, ethanol or propanol, higher alcohols such as ethylene glycol or polyether polyols and ether alcohols such as butyl glycol or methoxypropanol. Preferably the content of an organic solvent is no more than 5 percent by weight (based on component (C), more preferably no more than 1 percent by weight (based on component (C), in particular no more than 0.1 percent by weight, based on component (C).

Depending on the intended use of the non-living material to be treated the formulation according to the present invention may further comprise one or more components or additives (D) selected from preservatives, detergents, fillers, impact modifiers, anti-fogging agents, blowing agents, clarifiers, nucleating agents, coupling agents, fixative agents, cross-linking agents, conductivity-enhancing agents (anti-stats), stabilizers such as antioxidants, carbon and oxygen radical scavengers and peroxide decomposing agents and the like, flame retardants, mould release agents, agents having UV protecting properties, spreading agents, anti-blocking agents, anti-migrating agents, foam-forming agents, anti-soiling agents, thickeners, further biocides, wetting agents, plasticizers and film-forming agents, adhesive or anti-adhesive agents, optical brightening (fluorescent whitening) agents, pigments and dyestuffs.

A typical amount of the polymeric binder (B) is from 0.01 to 10 percent by weight (dry weight) of the (dry) weight of the material. As a general guideline, the weight ratio between insecticide and binder (B) should approximately be constant with a value depending on the insecticidal and migratory ability of the insecticide, i.e. the higher the amount the insecticide the higher also the amount of binder (B). Preferred amounts of binder (B) are from 0.1 to 5 percent by weight, more preferably 0.2 to 3 percent by weight of the (dry) weight of the material.

The coated material can comprise at least one pigment and/or at least one dyestuff. The amount of the at least one pigment and/or dyestuff is in general from 0.05 to 10 percent by weight, preferably 0.1 to 5 percent by weight, more preferably 0.2 to 3.5 percent by weight of the (dry) weight of the material.

The method of coating or treating the non-living material is not limited to a specific technology. Coating may be performed by dipping or submerging the non-living substrate into the formulation or by spraying the formulation onto the surface of the non-living material. After treating the treated non-living substrate may be dried simply at ambient temperatures.

Accordingly, no sophisticated technology is necessary for the coating, and therefore the coating process may be carried out by the end-user itself in at low-scale.

For instance, a typical end-user may coat/treat a net itself, e.g., within its household, using the formulation according to the present invention. For this purpose, it is in particular advantageous to use a kit as herein defined.

In an embodiment, the present invention provides a polymer, a fibre, a thread, a yarn, a net or weave comprising one or more compounds M of the invention, where also incorporated can be one or more other customary materials used to make such a polymer, and the polymer, a fibre, a thread, a yarn, a net or weave optionally can further incorporate one or more other insecticides and/or synergists.

In an embodiment, the present invention provides a net or weave incorporated with one or more compounds M, which optionally further incorporates one or more other insecticides and/or synergists.

As described in the art, a compound useful in the methods and other aspects of the present invention can be used alone or in combination with another insecticide, synergist, insect repellent, chemosterilant, flame retardant, UV protector/absorber, and/or additives for controlling release characteristics.

When used in accordance with the invention, the compound of the first aspect may be used alone to control a mosquito or used in combination with one or other known insecticides and/or one or more additives (such as synergists)—in polymers for making non-living substrates, such as nets and weaves, for formulations for treating non-living substrates, such as nets and weaves, in IRS products and space-spraying products.

In an embodiment, the present invention provides a composition (useful for coating a polymeric material or a product therefrom, or a useful as a spray product) comprising one or more compounds of the invention, which optionally further comprises one or more other insecticide and/or synergists and one or more other additives.

Examples of synergists are piperonylbutoxide (PBO), sebacic esters, fatty acids, fatty acid esters, vegetable oils, esters of vegetable oils, alcohol alkoxylates and antioxidants.

Suitable sebacic esters are for example dimethyl sebacate, diethyl sebacate, dibutyl sebacate, dibenzyl sebacate, bis(N-succinimidyl)sebacate, bis(2-ethylhexyl)sebacate, bis(1-octyloxy-2,2,6,6-tetramethyl-4-piperidyl)sebacate, bis(2,2,6,6-tetramethyl-4-piperidyl)sebacate and bis(1,2,2,6,6-pentamethyl-4-piperidinyl)sebacate (BLS292).

Suitable fatty acids are (preferably mono- or polyunsaturated) fatty acids having a chain length of 12 to 24 carbon atoms, for example palmitoleic acid, oleic acid, elaidic acid, vaccenic acid, icosenic acid, cetoleic acid, erucic acid, nervonic acid, linoleic acid, alpha-linolenic acid, gamma-linolenic acid, arachidonic acid, timnodonic acid, clupanodonic acid and cervonic acid. Particular preference is given to oleic acid, linoleic acid, alpha-linolenic acid and gamma-linolenic acid.

Suitable fatty acid esters are preferably methyl or ethyl esters of the above-recited fatty acids. Methyl esters are particularly preferred. Fatty acids and their esters can each also be present in mixtures.

Useful vegetable oils include all plant-derivable oils customarily usable in agrochemical compositions. As examples there may be mentioned sunflower oil, rapeseed oil, olive oil, castor oil, colza oil, maize kernel oil, cottonseed oil and soybean oil. Rapeseed oil is preferred.

Suitable esters of vegetable oils are methyl or ethyl esters of the above-recited oils. Methyl esters are preferred.

Antioxidants useful as additives include for example butylhydroxytoluene, butylhydroxyanisole and L-ascorbic acid.

Plant essential oils may also be used in an indoor residual spray compositions; examples are those selected from citronella, peppermint oil, d-limonene and *Abies sibirica* oil. These plant essential oil materials are known and used for other uses and can be prepared by a skilled artisan by employing known methods and also are available commercially.

In addition to the compound of the first aspect, the methods, compositions, polymer, product, substrate and/or vector control management methods/products according to the invention may contain one or more further insecticidally active ingredients. Particularly examples are one or more active ingredients from the class of organophosphates, pyrethroids, carbamates or neonicotinoids, and also DDT, indoxacarb, nicotine, bensultap, cartap, spinosad, camphechlor, chlordane, endosulfan, gamma-HCH, HCH, heptachlor, lindane, methoxychlor, acetoprole, ethiprole, fipronil, pyrafluprole, pyriprole, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine, diafenthiuron, azocyclotin, cyhexatin, fenbutatin-oxide, chlorfenapyr, binapacyrl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, *Bacillus thuringiensis* strains, spirodiclofen, spiromesifen, spirotetramat, 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8), flonicamid, amitraz, propargite, flubendiamide, chloranthraniliprol, thiosultap-sodium, azadirachtin, *Bacillus* spec., *Beauveria* spec., *Metarrhizium* spec., *Paecilomyces* spec., *Thuringiensin, Verticillium* spec., aluminium phosphide, methylbromide, sulfurylfluoride, cryolite, flonicamid, pymetrozine, clofentezine, etoxazole, hexythiazox, amidoflumet, benclothiaz, benzoximate, bifenazate, bromopropylate, buprofezin, chinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonylbutoxide, kaliumoleat, pyridalyl, sulfluramid, tetradifon, tetrasul, triarathene, verbutin, 4-(trifluoromethyl)pyridine-3-carboxamide, broflanilide, chloropenpyr, diflumetorim, fluazinam, thiocyclam, and thiocyclam hydrogen oxalate. In an embodiment, a preferred mixing partner is a pyrethroid, such as alpha-cypermethrin, bifenthrin, cyfluthrin, permethrin, deltamethrin, lambda-cyhalothrin and etofenprox, or 4-(trifluoromethyl)pyridine-3-carboxamide.

In a further aspect, a method of controlling mosquitoes, preferably mosquito vectors of pathogenic disease, which comprises contacting a mosquito or its environment with a composition comprising a mosquitocidally effective amount of the compound of the first aspect, is made available.

The present invention also provides a method comprising: (i) identifying a locus of potential or known interaction between a mosquito vector and a mammal, including a human, susceptible to pathogenic disease infection when contacted by such vector and (ii) positioning a vector control management or control product at the locus, wherein the product includes a mosquitocidally effective amount of the compound of the first aspect.

In a further aspect, the present invention provides a method for protecting a mammal, including a human, against mosquitoes, the method comprising applying to the mosquito or to a locus of potential or known interaction between the mammal and the mosquito, a vector control management product comprising a mosquitocidally effective amount of the compound of the first aspect.

Another aspect of the invention is a method for controlling the spread of a vector-borne disease comprising: identifying a mosquito vector; and contacting the mosquito vector or its environment with a vector control management method comprising a mosquitocidally effective amount of the compound of the first aspect.

An aspect of the invention also includes a mosquitocidal method which comprises contacting a mosquito or its environment with a vector control management product comprising a mosquitocidally effective amount of the compound of the first aspect.

The present invention through control of mosquitoes would also be expected to control the many viruses carried by such vectors. As an example, control of the mosquitoes of the genus *Aedes* by use of the compound of the first aspect, as part of a vector control management or control method/product, may control the Zika infections. Examples of mosquitoes reported to spread the Zika virus are the *Aedes* mosquitoes, such as *Aedes aegypti* and *Aedes albopictus*. Accordingly, in an aspect, the present invention provide a method of controlling Zika virus infection, the compound of the first aspect is present in a mosquitocidally effective amount in the vicinity of *Aedes* mosquitoes, such as *Aedes aegypti* and *Aedes albopictus*. In the vicinity of the mosquitoes is meant areas where mosquitoes are likely to be present, such as in the environment in general, specifically in a room, or at the site of a mosquito biting an individual or mammal, for example, on the skin surface.

In each of the methods according to present invention, the vector control management, preferably mosquito control management, is preferably one or more of a composition, a product and a treated article, at least one of which comprises the compound of the first aspect.

Preferred further aspects of the present invention is a product, and a treated article (such as substrates or non-living materials) comprising the compound of the first aspect.

In an embodiment, the development of malaria can be reduced by the mosquito control defined in first aspect.

In an embodiment, the vector control management method or control product is a net incorporated with the compound of the first aspect; in another embodiment, the vector control management product is a composition for coating a net, which composition comprises the compound of the first aspect; in further embodiment, the vector control management product is a composition for spraying surfaces of a dwelling, which composition comprises the compound of the first aspect.

The vector control management method product can comprise a further insecticide and/or synergist.

Another aspect is a polymeric material incorporated with the compound of the first aspect, which material is useful for making substrate or non-living material, such as threads, fibres, yarns, pellets, nets and weaves.

The present invention also makes available
  a method of controlling mosquitoes, preferably mosquito vectors of pathogenic disease, with the compound of the first aspect;
  a kit for treating a fibre, yarn, net and weave by coating wash resistant insecticidal properties thereto comprising: a first sachet comprising a pre-measured amount the compound of the first aspect, and a second sachet comprising a pre-measured amount of at least one polymeric binder;
  a method for treating a fibre, yarn, net and weave by coating wash resistant insecticidal properties thereto comprising (i) preparing a treatment composition, which comprises the compound of the first aspect, (ii) treating said fibre, yarn, net and weave and (iii) drying the resulting treated a fibre, yarn, net and weave;
  a method of preparing a polymeric material impregnated the compound of the first aspect, which material is useful for making substrate or non-living material, such as threads, fibres, yarns, pellets, nets and weaves, which method comprises mixing a polymer with the defined compound at a temperature between 120 to 250° C.;
  a method for mosquito vector-control, in particular controlling mosquito vectors carrying pathogenic disease, which method comprises (a) applying an effective amount of a liquid composition comprising the compound of the first aspect, and a polymeric binder, and optionally, one or more other insecticides, and/or synergists, to a surface of a dwelling; and/or (b) placing a substrate or non-living material incorporated with the compound of the first aspect, and optionally an additive, one or more other insecticides, and/or synergists, within a dwelling; and
  a net incorporated with the compound of the first aspect having a biological activity in accordance with the WHOPES guidelines of a knockdown after 60 minutes of between 95 percent and 100 percent and/or a mortality after 24 hours of between 80 percent and 100 percent after 20 washes.

The disclosure in the present application makes available each and every combination of embodiments disclosed herein.

A "fibre" as used in the present invention refers only to a fine, threadlike piece, generally made of natural material, such as cotton, or jute.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The Examples which follow serve to illustrate the invention; they do not limit the invention. Temperatures are given in degrees Celsius; mixing ratios of solvents are given in parts by volume. 1H NMR measurements were recorded on a Brucker 400 MHz spectrometer, chemical shifts are given in ppm relevant to a TMS standard. Spectra measured in deuterated solvents as indicated. Either one of the LCMS and/or GCMS methods below was used to characterize the compounds. The characteristic LCMS values obtained for each compound were the retention time ("Rt", recorded in minutes) and the measured molecular ion (M+H)+. The characteristic GCMS values obtained for each compound were the retention time ("Rt", recorded in minutes) and the measured molecular ion (M)+.

LCMS and GCMS Methods:

Method A (LC-MS):

Spectra were recorded on a Mass Spectrometer from API 2000 Mass Spectrometer from Applied Biosystems (Single quadrupole mass spectrometer); Ionisation method: Electrospray; Polarity: positive ions. Capillary (kV) 5.5, DP(V) 50.00, Entrance Potential (V) 10, Focusing Potential (V) 400, Source Temperature (° C.) 200, Ion Source Gas1 (Psi) 40, Ion Source Gas 2 (Psi) 50, Curtain Gas (Psi) 40; Mass range: 100 to 800 amu; UV Wavelength range (nm): 220 to 260; Type of column: Zorbax Extend C18; Column length: 50 mm; Internal diameter of column: 4.6 mm; Particle Size: 5 micron/X-bridge C18; Column length: 50 mm; Internal diameter of column: 4.6 mm; Particle Size: 5 micron/Epic C18; Column length: 50 mm; Internal diameter of column: 4.6 mm; Particle Size: 5 micron.

Method Shimadzu Prominance with the following HPLC gradient conditions (Solvent A: 10 Mm $NH_4OAc$ in Water and Solvent B: Acetonitrile)

Flow rate: 1.2 ml/min

| TIME | MODULE | % A (Buffer) | % B ($CH_3CN$) |
|---|---|---|---|
| 0.01 | Pumps | 90 | 10 |
| 1.50 | Pumps | 70 | 30 |
| 3.00 | Pumps | 10 | 90 |
| 4.00 | Pumps | 10 | 90 |
| 5.00 | Pumps | 90 | 10 |
| 5.10 | System Controller | Stop | |

Method B (GC-MS):

Spectra were recorded on a Mass Spectrometer from Agilent 6890 and 5973N MSD series instrument; Column: HP-5MS (30×250 μm×0.25 μm); Carrier Gas: Helium; Inlet Temperature: 250° C.; Split ratio: 20:1; Carrier Gas flow: 1.0 ml/min. Ramp Profile: Oven temperature initial from 60° C. held for 2 min then, 100° C. increasing at the rate of 20° C. held for 2 min, 310° C. increasing at the rate of 40° C. held for 4 min. Total run time is 15.25 min.

Method C (LC-MS):

UPLC1, Standard_Long gradient Column 1; ACQUITY SQD Mass Spectrometer from Waters (Single quadrupole mass spectrometer); Ionisation method: Electro spray; Polarity: positive ions; Capillary (kV) 3.00, Cone (V) 40.00, Extractor (V) 3.00, Source Temperature (° C.) 150, Desolvation Temperature (° C.) 400, Cone Gas Flow (L/Hr) 50, Desolvation Gas Flow (L/Hr) 750; Mass range: 100 to 800 Da; DAD Wavelength range (nm): 210 to 400; Method Waters ACQUITY UPLC with the following HPLC gradient conditions; (Solvent A: 0.05% Formic acid in water and Solvent B: 0.05% Formic acid in Acetonitrile:water 90:10); Type of column: YMC TRIART; Column length: 33 mm; Internal diameter of column: 2.1 mm; Particle Size: 1.8 micron; Temperature: 50° C. Flow rate: 1.5 ml/min

| TIME | MODULE | % A (Buffer) | % B (0.05% Formic acid in Acetonitrile:water 90:10) |
|---|---|---|---|
| 0.00 | Pumps | 98 | 2 |
| 0.75 | Pumps | 98 | 2 |
| 1.00 | Pumps | 90 | 10 |
| 2.00 | Pumps | 2 | 98 |
| 2.25 | Pumps | 2 | 98 |
| 2.90 | Pumps | 98 | 2 |
| 3.00 | Pumps | 98 | 2 |

Method D (GC-MS):

Spectra were recorded on a Mass Spectrometer from HP6890 series; Column: Agilent J&W GC Column CP-Sil 8 CB Low Bleed/MS (30 m×0.25 mm×0.25 μm); Carrier Gas: Helium (7.06 psi); Carrier Gas flow: 1.0 ml/min; Split ratio: 25:1; Velocity: 36 cm/sec; Inlet Temperature: 250° C. (Heater Set Point: 280° C.); Solvent delay: 0.1 min. Ramp Profile: Oven temperature initial from 40° C. held for 10 min then, 140° C. increasing at the rate of 40° C. held for 10 min, 300° C. increasing at the rate of 50° C. held for 5 min. Total run time is 30.70 min.

The compound of the invention can be distinguished from other similar compounds by virtue of greater efficacy at low application rates, which can be verified by the person skilled in the art using the experimental procedures outlined in the Examples below, using lower concentrations if necessary, for example 10 ppm, 5 ppm, 2 ppm, 1 ppm or 0.2 ppm; or lower application rates, such as 300, 200 or 100, mg of AI per m2.

EXAMPLES

Preparation Examples

Example 1: Preparation of Methyl (E)-2-[2-[4-chloro-5-(trifluoromethyl)thiazol-2-yl]oxyphenyl]-3-methoxy-prop-2-enoate (Compound of Formula I)

Step 1: 2,4-dichloro-5-(trichloromethyl)thiazole IX

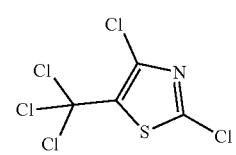

(IX)

To a stirred mixture of 2-chloro-5-(chloromethyl)thiazole X (200 g, 1.197 mol) and AIBN (9.8 g, 0.05 mol, 0.05 eq) at 130° C. chlorine gas was purged slowly and heating was continued for 24 hours, then AIBN (3.94 g, 0.024 mol, 0.02 eq) was added and the mixture was heated at 160° C. for another 24 hours. Chlorine gas purging was continued, AIBN (1.97 g, 0.012 mol, 0.01 eq) was added and the mixture was heated at 200° C. for 72 hours. Then the reaction was stopped after ~73% of the desired product IX had formed according to HPLC and GC-MS.

Dichlormethane (1.5 L) was added and the organic layer was washed with water (2×500 ml) and brine (1×500 ml), dried over anhydrous Na$_2$SO$_4$, filtered and concentrated to obtain a residue of 331 g. The crude mixture was adsorbed on silica-gel and purified through silica-gel column using hexane and dichloromethane. Four fractions were isolated and all fractions contained the desired product IX. Fraction 1 weighed 28 g, fraction 2 weight 135 g, fraction 3 weighed 80 g and fraction 4 weighed 65 g. According to the analytical data fraction 2 contained product IX (42%) of high purity. Analytics of Fraction 2:

$^1$H-NMR (400 MHz, CDCl$_3$), δ (ppm): no impurities observed.

GC-MS: t$_R$ 9.3 min; m/z=269/271/273/275, [M]$^+$. Method B.

Step 2: 2,4-dichloro-5-(trifluoromethyl)thiazole IIIa

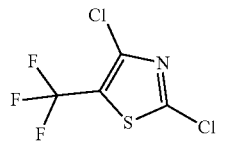

(IIIa)

2,4-dichloro-5-(trichloromethyl)thiazole IX (20.06 g; assay 97.5%; 72.2 mmol) was charged to a Hasteloy C autoclave. Subsequently, 18.8 ml of pyridine.HF (70% HF; 723.8 mmol, 10 equiv) was added. The system was flushed three times with nitrogen (2-4 bar) and subsequently pressurized with nitrogen (4 bar). Stirring was started (500-700 rpm) and the autoclave was heated to an internal temperature of 140° C. The mixture was stirred for five hours at this temperature and subsequently cooled to approximately 30° C. The mixture was quenched with 50% aqueous KOH. After cooling, the autoclave was opened. The autoclave was emptied and subsequently rinsed with water and ethylacetate. The combined rinse liquid and reaction mixture was extracted with EtOAc. The GC-analysis revealed a fairly clean conversion of the 2,4-dichloro-5-(trichloromethyl)thiazole IX to primarily 2,4-dichloro-5-(trifluoromethyl)thiazole IIIa. The assay yield was determined by quantitative 19F-NMR to be 84.5%. The ethylacetate solution was washed three times with dilute aqueous HCl (pH=2.5) in order to remove pyridine. The bulk of the ethylacetate was removed on a rotary evaporator and the residue was distilled to give 8.4 g (52%) of 2,4-dichloro-5-(trifluoromethyl)thiazole IIIa.

$^{19}$F-NMR (282.4 MHz, CDCl$_3$), δ (ppm): −55.14 (CF$_3$).
GC-MS: t$_R$ 11.8 min; m/z=221, 223, 225, [M]$^+$. Method D.
B.p.: 160° C., determined by DSC.

Step 3: Methyl 2-[2-[4-chloro-5-(trifluoromethyl) thiazol-2-yl]oxyphenyl]-3,3-dimethoxy-propanoate V

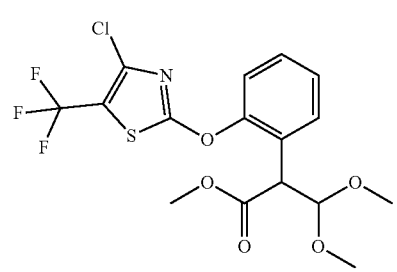

(V)

To a stirred solution of methyl 2-(2-hydroxyphenyl)-3,3-dimethoxy-propanoate VI (7.50 g, 31.21 mmol; prepared as described in DE 19525393) in DMF (25 ml) at room temperature was added 2,4-dichloro-5-(trifluoromethyl)thiazole (9.5 g, 1.1 eq., 34.5 mmol), K$_2$CO$_3$ (8.62 g, 2 eq., 62.4 mmol) and DABCO (350 mg, 3.12 mmol, 0.1 eq). The mixture was stirred at room temperature for 15 hours. Water was added and the mixture was extracted with ethylacetate. The organic phase was washed with water and brine, dried over anhydrous Na$_2$SO$_4$, filtered, concentrated and purified through column chromatography. 4.8 g (11.3 mmol, 36%) of pure methyl 2-[2-[4-chloro-5-(trifluoromethyl)thiazol-2-yl] oxyphenyl]-3,3-dimethoxy-propanoate was obtained along with 1.56 g of a mixture containing the mainly the desired product V.

$^1$H-NMR (400 MHz, CDCl$_3$), δ (ppm): 3.12 (s, 3H), 3.42 (s, 3H), 3.61 (s, 3H), 4.26 (d, 1H); 4.97 (d, 1H), 7.28 (d, 1H), 7.32-7.42 (m, 2H), 7.65 (dd, 1H).
$^{19}$F-NMR (376 MHz, CDCl$_3$), δ (ppm): −54.56 (CF$_3$).

Step 4: Methyl (E)-2-[2-[4-chloro-5-(trifluoromethyl)thiazol-2-yl]oxyphenyl]-3-methoxy-prop-2-enoate (Compound of Formula I)

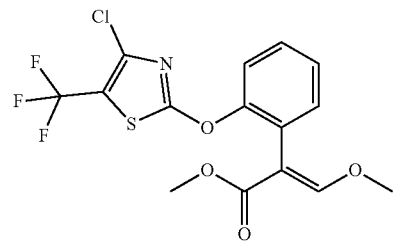

(I)

To a stirred solution of methyl 2-[2-[4-chloro-5-(trifluoromethyl)thiazol-2-yl]oxyphenyl]-3,3-dimethoxy-propanoate V (4.75 g, 11.15 mmol of previous step) in acetic anhydride (20 ml) methanesulfonic acid (0.5 ml; 0.34 g; 3.5 mmol, 0.3 eq) was added and the mixture was stirred at 50° C. for 3 hours. Saturated NaHCO$_3$ was added, stirred for 10 minutes and the mixture was extracted with ethylacetate. The organic layer was washed with water and brine, dried over anhydrous Na$_2$SO$_4$, filtered and concentrated. The residue was purified through combi-flash column chromatography using 15-25% ethylacetate in hexane to give 4.1 g (10.4 mmol, 93%) of the desired product of formula I.

$^1$H-NMR (400 MHz, CDCl$_3$), δ (ppm): 3.65 (s, 3H), 3.78 (s, 3H), 7.29-7.44 (m, 4H), 7.54 (s, 1H).
$^{19}$F-NMR (376 MHz, CDCl$_3$), δ (ppm): −54.47 (CF$_3$).
LC-MS: t$_R$ 3.69 min; m/z=394/396 (3:1), [M+H]$^+$. Method A.
M.p.: 77-79° C.

Example 2: Preparation of Methyl (E)-3-methoxy-2-[2-[5-(trifluoromethyl)thiazol-2-yl]oxyphenyl]-prop-2-enoate (Compound of Formula II)—Starting from Compound of Formula I

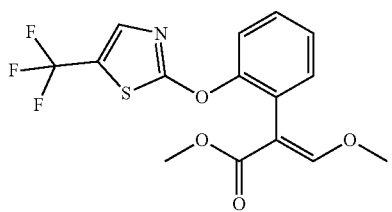
(II)

To a stirred solution of (E)-2-[2-[4-chloro-5-(trifluoromethyl)thiazol-2-yl]oxyphenyl]-3-methoxy-prop-2-enoate I (110 mg, 0.28 mmol) in ethylacetate (8 ml) were added 5 mol % Pd/C and ammonium formate (176.4 mg, 2.8 mmol, 10 eq) and the mixture was heated at 70° C. After 54 hours further 10 eq ammonium formate and 1 mol % Pd/C were added and heating at 70° C. was continued. After 80 hours further 5 eq of ammonium formate and 1 mol % Pd/C were added and heating at 70° C. was continued. After 104 hours the reaction mixture was cooled and filtered. The filtrate was purified through combiflash column using 15-20% ethylacetate in hexane. 81 mg (0.225 mmol, 81%) of the desired product of formula II were obtained.

$^1$H-NMR (400 MHz, CDCl$_3$), δ (ppm): 3.62 (s, 3H), 3.75 (s, 3H), 7.29-7.37 (m, 2H), 7.37-7.43 (m, 2H), 7.51-7.54 (m, 2H).
$^{19}$F-NMR (376 MHz, CDCl$_3$), δ (ppm): −55.42 (CF$_3$).
LC-MS: t$_R$ 3.85 min; m/z=360, [M+H]$^+$. Method A.

Example 3: Preparation of Methyl (E)-3-methoxy-2-[2-[5-(trifluoromethyl)thiazol-2-yl]oxyphenyl]-prop-2-enoate (Compound of Formula II)—Using Compound of Formula XII as an Intermediate Step 1 (Procedure 1): Methyl 3,3-dimethoxy-2-[2-[5-(trifluoromethyl)thiazol-2-yl]oxyphenyl]propanoate XII

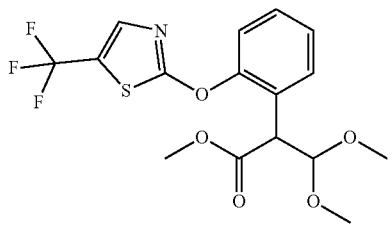
(XII)

To a stirred solution of methyl 2-[2-[4-chloro-5-(trifluoromethyl)thiazol-2-yl]oxyphenyl]-3,3-dimethoxy-propanoate V (100 mg, 0.235 mmol) in 5 ml ethylacetate 5 mol % Pd/C (50% moisture) and ammonium formate (2.1 eq) were added and the mixture was stirred at 70° C. for 96 hours. The reaction mixture was filtered through celite and extracted with ethylacetate. The organic phase was washed with water and brine, dried over anhydrous Na$_2$SO$_4$, filtered and concentrated. The residue was purified through combi-flash column using 5-10% ethylacetate/hexane. 42 mg (0.107 mmol, 46%) of the desired product XII were obtained.

$^1$H-NMR (400 MHz, CDCl$_3$), δ (ppm): 3.17 (s, 3H), 3.42 (s, 3H), 3.59 (s, 3H), 4.32 (d, 1H), 4.99 (d, 1H), 7.27-7.41 (m, 3H), 7.54 (s, 1H), 7.65 (d, 1H).
$^{19}$F-NMR (376 MHz, CDCl$_3$), δ (ppm): −54.44 (CF$_3$).
LC-MS: t$_R$ 3.55 min; m/z=392, [M+H]$^+$. Method A.

Step 1 (Procedure 2): Methyl 3,3-dimethoxy-2-[2-[5-(trifluoromethyl)thiazol-2-yl]oxyphenyl]propanoate XII

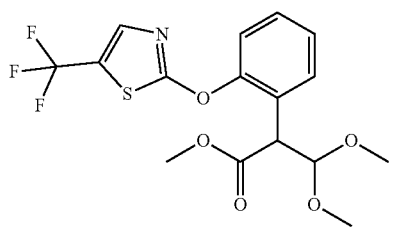
(XII)

To a stirred solution of methyl 2-(2-hydroxyphenyl)-3,3-dimethoxy-propanoate VI (1 g, 4.16 mmol; prepared as described in DE 19525393) in dry DMF (5 ml) was added under cooling 2-chloro-5-(trifluoromethyl)thiazole XIa (780.3 mg, 4.16 mmol, 1 eq, prepared as described in WO 2012089606). Then DABCO (0.1 eq) and K$_2$CO$_3$ (2.2 eq) were added and the mixture was stirred at room temperature for 16 hours. Water was added and the mixture was extracted with ethylacetate. The organic phase was dried over anhydrous Na$_2$SO$_4$, filtered and concentrated. The residue was purified through silica-gel column chromatography using 10-20% ethylacetate in hexane. 1.31 g (2.91 mmol, 81%) of the desired product XII were obtained.

$^1$H-NMR (400 MHz, CDCl$_3$), δ (ppm): 3.17 (s, 3H), 3.42 (s, 3H), 3.59 (s, 3H), 4.32 (d, 1H), 4.99 (d, 1H), 7.27-7.41 (m, 3H), 7.54 (s, 1H), 7.65 (d, 1H).
$^{19}$F-NMR (376 MHz, CDCl$_3$), δ (ppm): −54.44 (CF$_3$).
LC-MS: t$_R$ 3.62 min; m/z=392, [M+H]$^+$. Method A.

Step 2: Methyl (E)-3-methoxy-2-[2-[5-(trifluoromethyl)thiazol-2-yl]oxyphenyl]-prop-2-enoate (Compound of Formula II)

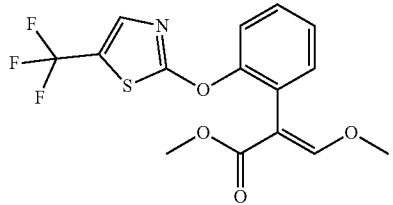
(II)

To a stirred solution of methyl 3,3-dimethoxy-2-[2-[5-(trifluoromethyl)thiazol-2-yl]oxyphenyl]-propanoate XII (500 mg, 1.27 mmol) in acetic anhydride (1 ml) methanesulfonic acid (150 mg) was added and the mixture was stirred at 50° C. for 3 hours. Saturated aqueous NaHCO₃ solution was added. The mixture was stirred for 10 minutes and extracted with ethylacetate. The organic layer was washed with water and brine, dried over anhydrous Na₂SO₄, filtered and concentrated. The residue was purified through combi flash column chromatography using 10-20% ethylacetate/hexane. 417 mg (1.16 mmol, 91%) of the desired product of the formula II were obtained as a gum.

$^{1}$H-NMR (400 MHz, CDCl₃), δ (ppm): 3.62 (s, 3H), 3.75 (s, 3H), 7.29-7.37 (m, 2H), 7.37-7.43 (m, 2H), 7.51-7.54 (m, 2H).
$^{19}$F-NMR (376 MHz, CDCl₃), δ (ppm): −55.42 (CF₃).
LC-MS: $t_R$ 3.83 min; m/z=360 [M+H]⁺. Method A.

Example 4: Preparation of 2-chloro-5-(trifluoromethyl)thiazole (Compound of Formula XIa)

Step 1 (Procedure 1): 2-chlorothiazole-5-carboxylic Acid (Compound of Formula XIV) Starting from 2-chloro-5-(chloromethyl)thiazole (Compound of Formula X)

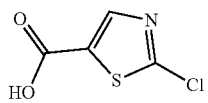
(XIV)

To a stirred solution of thiazole compound X (20.0 g, 119 mmol) in aq. H₂SO₄ (70%) (453.5 g) was added aq. HNO₃ (65%, 73.2 g) dropwise at 110° C. After stirring 12 hours at 110° C. the starting material was consumed. The reaction mixture was poured into water and extracted with ethyl acetate, dried over anhydrous Na₂SO₄ and concentrated to give 14.8 g of crude product. The crude compound was dissolved in DCM-methanol, adsorbed on silica-gel and then purified using combiflash chromatography (10% methanol/90% dichloromethane). 14.2 g (86.8 mmol) of product XIV were obtained (yield 72.9%).

$^{1}$H-NMR (400 MHz, DMSO), δ (ppm): 8.22 (s, 1H), 13.9 (broad s, 1H).
$^{13}$C-NMR (100 MHz, DMSO), δ (ppm): 133.00, 146.32, 155.13, 160.87.
LC-MS: $t_R$ 1.05 min; m/z=164/166 [M+H]⁺. Method C.

Step 1 (Procedure 2): 2-Chlorothiazole-5-carboxylic Acid (Compound of Formula XIV) Starting from (2-chlorothiazol-5-yl)methanol (Compound of Formula XVI)

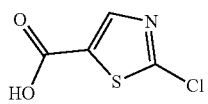
(XIV)

To a stirred solution of thiazole compound XVI (1 g, 6.68 mmole) in aq. H₂SO₄ (70%) (26 g) was added aq. HNO₃ (65%, 4 g) dropwise at 110° C. After stirring 1 hour at 110° C. the starting material was consumed. The reaction mixture was poured into the crust ice and extracted with ethyl acetate (3×20 ml). The combined organic phases were dried over anhydrous Na₂SO₄, and concentrated. The was purified by column chromatography (70% ethyl acetate; 30% hexane) 810 mg (4.95 mmol) of the product XIV was obtained as a white solid (yield 74%).

$^{1}$H-NMR (400 MHz, DMSO), δ (ppm): 8.24 (s, 1H), 13.8 (broad s, 1H).

Step 1 (Procedure 3): 2-Chlorothiazole-5-carboxylic Acid (Compound of Formula XIV) Starting from 2-chlorothiazole-5-carbaldehyde (Compound of Formula XVII)

To a stirred solution of thiazole compound XVII (1 g, 6.78 mmole) in aq. H₂SO₄ (70%) (26 g) was added aq. HNO₃ (65%, 4 g) dropwise at 110° C. After stirring 1 hour at 110° C. the starting material was consumed. The reaction mixture was poured into water and extracted with ethyl acetate (3×20 ml). The combined organic phases were dried over anhydrous Na₂SO₄, and concentrated. The was purified by combiflash chromatography (70% ethyl acetate; 30% hexane) to give 870 mg (5.32 mmol) of the product XIV (yield 78%).

$^{1}$H-NMR (400 MHz, DMSO), δ (ppm): 8.23 (s, 1H), 13.9 (broad s, 1H).

Step 2: 2-Chloro-5-(trichloromethyl)thiazole (Compound of Formula XIII)

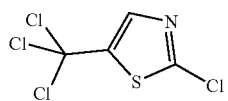
(XIII)

A stirred solution of 2-chlorothiazole-5-carboxylic acid (compound of formula XIV) (25 g, 152.8 mmol) in thionyl chloride (54.54 g, 458 mmol, 3 eq) and a catalytic amount of DMF were heated at 110° C. for 16 hours. Then excess thionyl chloride was removed to give 28.3 g of crude 2-chlorothiazole-5-carbonyl chloride XV. In a sealed tube PCl₅ (102 g, 489 mmol, 3.2 eq) was added to the acid chloride and the mixture was heated at 190° C. for 48 hours. The reaction mixture was slowly poured into ice water keeping the temperature below 10° C. The flask was washed with dichloromethane and the aqueous phase was extracted with dichloromethane (3×200 ml). The combined organic phases were washed with water (1×100 ml) and brine (1×100 ml), dried over anhydrous Na₂SO₄ and concentrated to give 42.5 g of crude material. The residue was dissolved in 100 ml dichloromethane, 100 ml 10% NaOH solution was added, and the mixture was stirred for 1 hour. The phases were separated and the aqueous phase was extracted with dichloromethane. The combined organic phases were washed with water and brine, dried over anhydrous Na₂SO₄, and concentrated. The residue was purified through silica gel column using hexane as an eluent. 22.2 g (92.7 mmol) of product XIII were obtained (yield 61.3%).

$^1$H-NMR (400 MHz, CDCl$_3$), δ (ppm): 7.84 (s, 1H).

GC-MS: t$_R$ 8.54 min; m/z=235, 237, 239, 241 [M]$^+$. Method B.

The acidic aqueous phase from the first extraction (pH~1) was extracted with ethyl acetate (2×100 ml). The basic aqueous phase from the second extraction was acidified with concentrated HCl (pH~2) and then extracted with ethyl acetate. The combined organic phases were dried over anhydrous Na$_2$SO$_4$ and concentrated to give 4.4 g of recovered acid (compound of formula XIV) as an off-white solid.

Step 3: 2-Chloro-5-(trifluoromethyl)thiazole (Compound of Formula XIa)

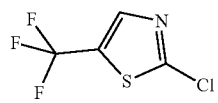
(XIa)

2-Chloro-5-(trichloromethyl)thiazole (compound of formula XIII) (4.9 g; assay, 20.4 mmol) was charged in a Hasteloy C autoclave. Subsequently, 4.33 ml of pyridine.HF (70% HF; 167 mmol=8 eq) was added. The system was flushed three times with nitrogen (2-4 bar) and subsequently pressurized with nitrogen (4 bar). Stirring was started (500-700 rpm) and the autoclave was heated to an internal temperature of 140° C. The mixture was stirred for five hours at this temperature and subsequently cooled to approximately 33° C. The mixture was quenched with 50% aq. KOH (20.0 g). After cooling, the autoclave was opened. The autoclave was emptied and subsequently rinsed with water (5 ml) and dichloromethane (20 ml). The combined rinse liquid and reaction mixture was extracted with dichloromethane (2×20 ml). The aqueous phase was back extracted with dichloromethane (3×10 ml). The combined organic phases, were analyzed by GC and 19F-NMR. The predominant reaction product was found to be 2-chloro-5-(trifluoromethyl)thiazole (compound of formula XIa) (44% yield; based on 19F-NMR). Pyridine was removed by washing the solution with aquoues 1M HCl (1×20 ml; 1×10 ml) and the combined water layers were back extracted with dichloromethane (2×20 ml). The combined organic phases were concentrated and distilled using a Vigreux column to give pure 2-chloro-5-(trifluoromethyl)thiazole (compound of formula XIa).

$^1$H-NMR (400 MHz, CDCl$_3$), δ (ppm): 7.82 (s, 1H).

$^{19}$F-NMR (282.4 MHz, CDCl$_3$), δ (ppm): −55.22 (CF$_3$).

GC-MS: t$_R$ 5.2 min; m/z=187, 189, [M]$^+$. Method D.

Example 5: Preparation of Methyl (E)-3-methoxy-2-[2-[[4-(trifluoromethyl)-2-pyridyl]oxy]phenyl]prop-2-enoate (Compound of Formula XVIII)— Starting from Pyridine of Formula XXI

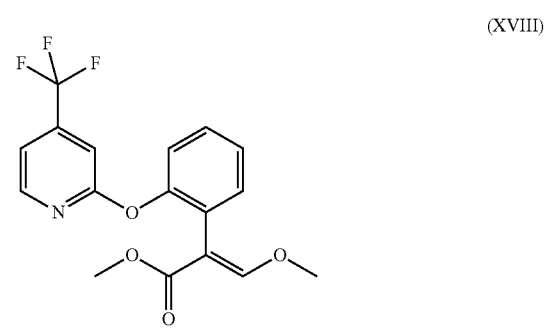 [SMILES: CO/C=C(/C(=O)OC)c1ccccc1Oc1cc(C(F)(F)F)ccn1]
(XVIII)

Step 1: Methyl 2-[2-[[6-chloro-4-(trifluoromethyl)-2-pyridyl]oxy]phenyl]-3,3-dimethoxy-propanoate XX

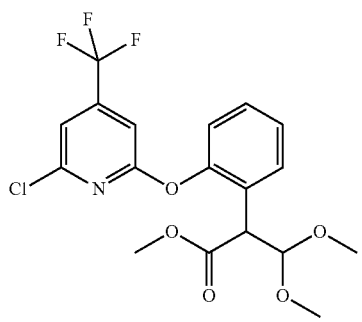
(XX)

To a stirred solution of methyl 2-(2-hydroxyphenyl)-3,3-dimethoxy-propanoate VI (10 g, 41.6 mmol; prepared as described in DE 19525393) in dry DMF (100 ml) was added K$_2$CO$_3$ (11.5 g, 83.2 mmol), DABCO (220 mg, 0.2 mmol) and 2,6-dichloro-4-(trifluoromethyl)pyridine XXIa (8.9 g, 40 mmol). After complete addition the reaction mixture was stirred at room temperature for 16 hours and monitored by TLC and LC-MS. After completion of conversion the reaction mixture was diluted with water and extracted with ethyl acetate (3×50 ml), the combined organic layer was washed with water, brine (once each), dried over anhydrous Na$_2$SO$_4$ and concentrated to yield crude compound XX. The crude compound XX was purified by combiflash using 5-10% ethyl acetate/hexane as an eluent to give 7.0 g the desired methyl 2-[2-[[6-chloro-4-(trifluoromethyl)-2-pyridyl]oxy]phenyl]-3,3-dimethoxy-propanoate XX.

$^1$H-NMR (400 MHz, CDCl$_3$), δ (ppm): 3.15 (s, 3H), 3.40 (s, 3H), 3.57 (s, 3H), 4.21 (d, 1H), 4.98 (d, 1H), 6.96 (s, 1H), 7.08 (d, 1H), 7.22 (s, 1H), 7.26-7.38 (m, 2H), 7.63 (dd, 1H).

LC-MS: t$_R$ 3.83 min; m/z=420, [M+H]$^+$. Method A.

Step 2: Methyl (E)-2-[2-[[6-chloro-4-(trifluoromethyl)-2-pyridyl]oxy]phenyl]-3-methoxy-prop-2-enoate XIX

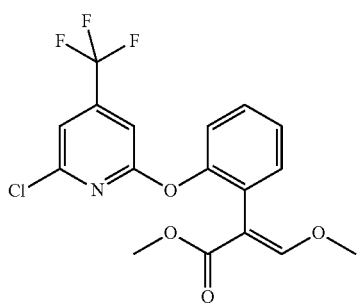

(XIX)

To a stirred solution of methyl 2-[2-[[6-chloro-4-(trifluoromethyl)-2-pyridyl]oxy]phenyl]-3,3-dimethoxy-propanoate XX (3.0 g, 7.15 mmol) in acetic anhydride (30 ml) methane sulfonic acid (0.14 ml) was added at room temperature. The mixture was stirred at 50° C. for 16 hours and then quenched with saturated aqueous NaHCO$_3$ solution. The mixture was extracted with ethylacetate (3×50 ml). The organic layer was dried over anhydrous Na$_2$SO$_4$, filtered and concentrated. The residue was purified by column chromatography using ethyl acetate/hexane as an eluent to give 2.0 g of the desired pure methyl (E)-2-[2-[[6-chloro-4-(trifluoromethyl)-2-pyridyl]oxy]phenyl]-3-methoxy-prop-2-enoate XIX.

$^1$H-NMR (400 MHz, CDCl$_3$), δ (ppm): 3.51 (s, 3H), 3.73 (s, 3H), 6.82 (s, 1H); 7.12-7.20 (m, 2H), 7.25-7.34 (m, 2H), 7.34-7.44 (m, 2H).

LC-MS: t$_R$ 3.66 min; m/z=388/390 [M+H]$^+$. Method A.

Step 3: Methyl (E)-3-methoxy-2-[2-[[4-(trifluoromethyl)-2-pyridyl]oxy]phenyl]prop-2-enoate XVIII

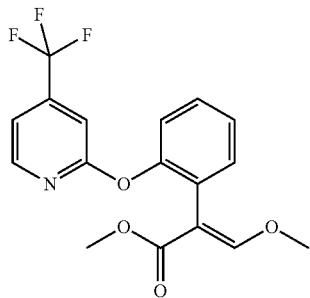

(XVIII)

To a stirred solution of methyl (E)-2-[2-[[6-chloro-4-(trifluoromethyl)-2-pyridyl]oxy]phenyl]-3-methoxy-prop-2-enoate XIX (2 g, 5.16 mmol) in methanol (35 ml) was added ammonium formate (650 mg, 10.32 mmol) and 10% Pd—C (928 mg, 0.88 mmol of palladium, 16 mol %, 0.16 eq) at room temperature. The mixture was heated to 60° C. and stirred for 2 hours. The reaction was monitored by TLC and LCMS and after complete consumption of compound XIX, the reaction mixture was cooled to room temperature and filtered through celite and concentrated under reduced pressure. The residue was partitioned between water and ethyl acetate. The organic layer was dried over anhydrous Na$_2$SO$_4$, filtered and concentrated to yield crude XVIII which was purified by column chromatography using ethyl acetate/hexane as an eluent to yield 1.9 g the desired methyl (E)-3-methoxy-2-[2-[[4-(trifluoromethyl)-2-pyridyl]oxy]phenyl]prop-2-enoate XVIII.

$^1$H-NMR (400 MHz, CDCl$_3$), δ (ppm): 3.55 (s, 3H), 3.70 (s, 3H), 6.99 (s, 1H); 7.12-7.20 (m, 2H), 7.25-7.41 (m, 3H), 7.42 (s, 1H), 8.32 (d, 1H).

LC-MS: t$_R$ 3.52 min; m/z=354 [M+H]$^+$. Method A (column Zorbax C18 4.6×50, 5u).

Example 6: Preparation of Methyl (E)-3-methoxy-2-[2-[[4-(trifluoromethyl)-2-pyridyl]oxy]phenyl]prop-2-enoate (Compound of Formula XVIII)—Starting from Pyridine of Formula XXVIa

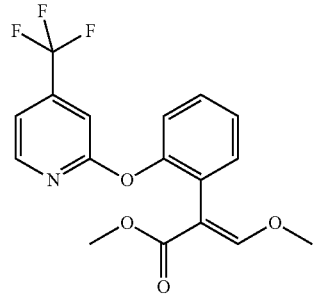

(XVIII)

Step 1: 2-[2-[[4-(trifluoromethyl)-2-pyridyl]oxy]phenyl]acetic Acid XXV

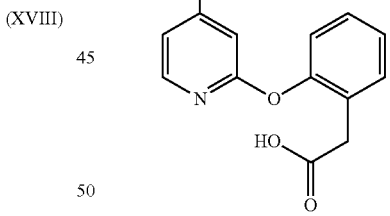

(XXV)

To a stirred solution of 2-(2-hydroxyphenyl)acetic acid XXVII (5 g, 32.86 mmol) and 2-chloro-4-trifluoromethylpyridine XXVIa (7.16 g, 39.43 mmol, 1.2 eq) in DMF (12.6 mL) in a round bottom flask fitted with a water condenser was added K$_2$CO$_3$ (11.3 g, 82.15 mmol, 2.5 eq) and the mixture was stirred at 150° C. for 16 hours. Then water was added (200 ml) to the reaction mixture. The mixture was stirred for 10 minutes and extracted with ethyl acetate (3×100 ml). The aqueous part was acidified using 6N HCl to pH~2, stirred for 5 minutes and then extracted with ethyl acetate (3×100 mL). The combined organic layer was washed with brine (3×150 ml), dried (Na$_2$SO$_4$), filtered and evaporated to dryness. The obtained solid was triturated (2 times) with hexane, decanted the solvent and dried in vacuum to give 2-[2-[[4-(trifluoromethyl)-2-pyridyl]oxy]

phenyl]acetic acid XXV as a brown solid. Crude Yield=8.2 g (84%; purity by quantitative NMR 88%). ¹H-NMR (400 MHz, DMSO), δ (ppm): 3.49 (s, 2H), 7.15 (d, 1H), 7.24 (t, 1H), 7.31-7.38 (m, 2H), 7.41 (d, 1H), 7.47 (d, 1H), 8.37 (d, 1H), 12.23 (s, 1H).

LC-MS: $t_R$ 2.40 min; m/z=298, [M+H]⁺. Method A.

Step 2, Procedure 1: Methyl 2-[2-[[4-(trifluoromethyl)-2-pyridyl]oxy]phenyl]acetate XXIII

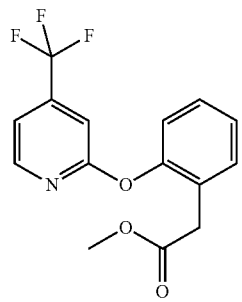

(XXIII)

To a stirred solution of 2-[2-[[4-(trifluoromethyl)-2-pyridyl]oxy]phenyl]acetic acid XXV (5 g, 16.83 mmol) in methanol (50 ml) was added methane sulfonic acid (162 mg, 0.1 eq) and the reaction was heated to reflux for 1 hour. The solvent was removed under reduced pressure and the residue was dissolved in 200 ml of ethyl acetate. The organic layer was washed with saturated NaHCO₃ solution (2×150 ml), brine (200 ml), dried (Na₂SO₄), filtered and concentrated to give methyl 2-[2-[[4-(trifluoromethyl)-2-pyridyl]oxy]phenyl]acetate XXIII as a brown liquid. Crude yield=5.1 g (97.5%).

¹H-NMR (400 MHz, CDCl₃), δ (ppm): 3.56 (s, 3H), 3.60 (s, 2H), 7.10 (d, 1H); 7.15 (s, 1H), 7.19 (d, 1H), 7.21-7.27 (m, 1H), 7.31-7.41 (m, 2H), 8.29 (d, 1H).

LC-MS: $t_R$ 3.50 min; m/z=312 [M+H]⁺. Method A (Zorbax C18 4.6×50, 5u).

Step 2, Procedure 2: Methyl 2-[2-[[4-(trifluoromethyl)-2-pyridyl]oxy]phenyl]acetate XXIII

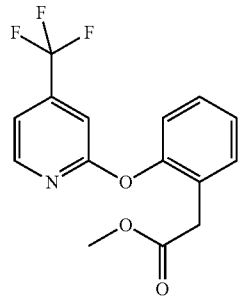

(XXIII)

To a stirred solution of the 2-[2-[[4-(trifluoromethyl)-2-pyridyl]oxy]phenyl]acetic acid XXV (2.9 g, 9.75 mmole) in DMF (5 ml) were added K₂CO₃ (2.7 g, 19.5 mmol) and dimethylsulphate (1.4 ml, 14.63 mmol) and the reaction was stirred for 5 hours at room temperature. Water was added (60 ml) to the reaction mixture. The mixture was stirred for 30 minutes and extracted with ethyl acetate (3×100 ml). The combined organic phase was washed with saturated NaHCO₃ (2×100 ml) and brine (2×100 ml), dried (Na₂SO₄), filtered and evaporated to give the crude compound as a brown liquid. The crude compound was purified by column chromatography using silica gel column and ethyl acetate-hexane (5-10%) as an eluent to give the desired methyl 2-[2-[[4-(trifluoromethyl)-2-pyridyl]oxy]phenyl]acetate XXIII as a yellow liquid (2.7 g).

¹H-NMR (400 MHz, CDCl₃), δ (ppm): 3.56 (s, 3H), 3.60 (s, 2H), 7.10 (d, 1H); 7.15 (s, 1H), 7.19 (d, 1H), 7.21-7.27 (m, 1H), 7.31-7.41 (m, 2H), 8.29 (d, 1H).

LC-MS: $t_R$ 3.81 min; m/z=312 [M+H]⁺. Method A (Epic c18 4.6×50, 5u).

Step 3, Procedure 1: Methyl (E)-3-hydroxy-2-[2-[[4-(trifluoromethyl)-2-pyridyl]oxy]phenyl]prop-2-enoate XXII

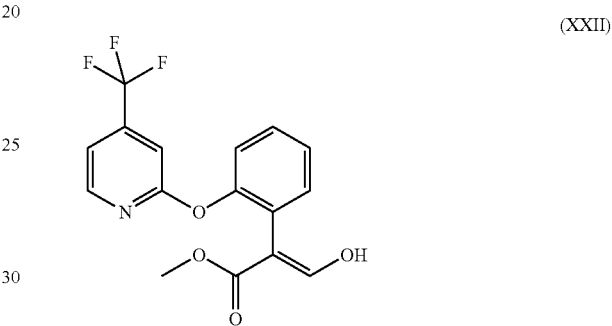

(XXII)

To a stirred solution of TiCl₄ (4.22 ml, 4.22 mmol, 1M solution in toluene) in CH₂Cl₂ (3 ml) at 0° C. was added methyl formate (0.3 ml, 4.82 mmol) at 0° C. The mixture was stirred for 15 minutes at 0° C.-5° C. A solution of methyl 2-[2-[[4-(trifluoromethyl)-2-pyridyl]oxy]phenyl]acetate XXIII (1 g, 3.21 mmol) in CH₂Cl₂ (3 mL) was added to the above mixture at 0°-5° C. The mixture was stirred for 30 minutes at 0° C.-5° C. Triethyl amine (1.12 ml, 8.03 mmol) was then added to the reaction mixture during 30 minutes at 0° C. Stirring was continued for 1 hour at 0° C.-5° C. The reaction was quenched by carefully adding water (7 ml) at 5°-15° C. and the temperature slowly raised to room temperature during 20 minutes. Then the organic layer was separated.

Step 4, Procedure 1: Methyl (E)-3-hydroxy-2-[2-[[4-(trifluoromethyl)-2-pyridyl]oxy]phenyl]prop-2-enoate XVIII

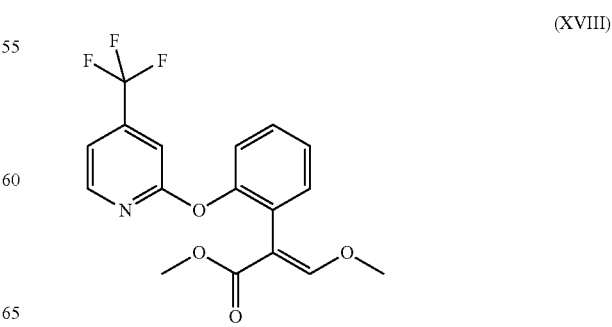

(XVIII)

To the organic layer of step 3 (procedure 1) were added 7.6 g of 10.6% aqueous $Na_2CO_3$, dimethyl sulphate (0.46 mL, 4.82 mmol) and tetrabutyl ammonium hydrogen sulphate (109 mg, 0.32 mmol) at room temperature. The reaction mixture was stirred for 1 hour at 25° C.-30° C. The organic layer was separated and $Na_2S_2O_3.5H_2O$ (1.6 g, 40% aqueous solution) was added. The mixture was then stirred for 2 hours at 25-30° C. The organic layer was separated and the aqueous part was washed with dichloromethane. The combined organic phases were dried ($Na_2SO_4$), filtered and concentrated to give the crude compound XVIII. The crude compound XVIII was purified by silica gel column chromatography using ethyl acetate 15-20%/hexane as an eluent. The solvent was evaporated under reduced pressure to afford 1.0 g of methyl (E)-3-hydroxy-2-[2-[[4-(trifluoromethyl)-2-pyridyl]oxy]phenyl]prop-2-enoate XVIII as a sticky liquid.

$^1$H-NMR (400 MHz, $CDCl_3$), δ (ppm): 3.55 (s, 3H), 3.70 (s, 3H), 6.99 (s, 1H); 7.12-7.20 (m, 2H), 7.25-7.41 (m, 3H), 7.42 (s, 1H), 8.32 (d, 1H).

LC-MS: $t_R$ 3.72 min; m/z=354 [M+H]$^+$. Method A (Epic c18 4.6×50, 5u).

Step 3, Procedure 2: Methyl (Z)-3-(dimethyl-amino)-2-[2-[[4-(trifluoromethyl)-2-pyridyl]oxy]phenyl]prop-2-enoate XXIV

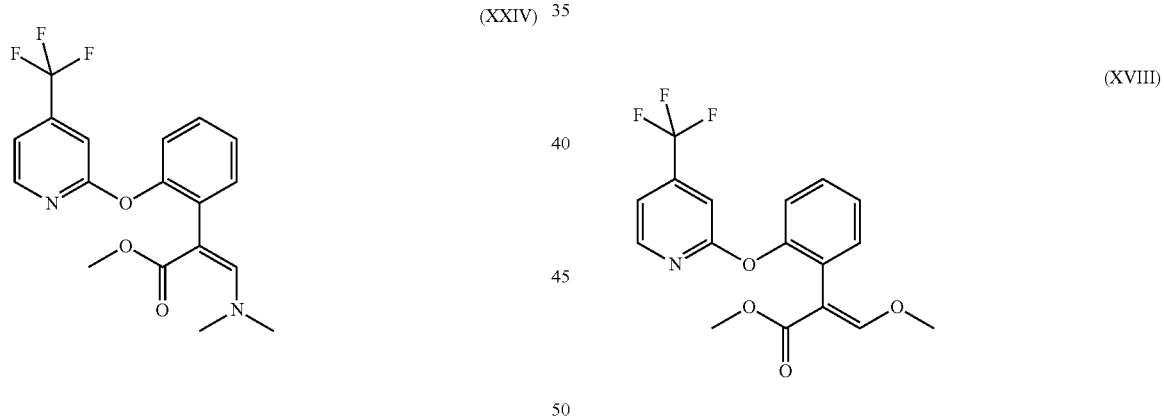

(XXIV)

To a stirred solution of methyl 2-[2-[[4-(trifluoromethyl)-2-pyridyl]oxy]phenyl]acetate XXIII (5 g, 16.06 mmol) in DMF (15 ml) was added DMF-DMA (4.3 ml, 32.12 mmol, 2 eq) and the mixture was heated at 150° C. for 16 hours. The solvent was evaporated under reduced pressure. Crude Yield of methyl (Z)-3-(dimethylamino)-2-[2-[[4-(trifluoromethyl)-2-pyridyl]oxy]phenyl]prop-2-enoate XXIV was 5.5 g (yield=93.5%, purity by quantitative NMR: 91%).

$^1$H-NMR (400 MHz, $CDCl_3$), δ (ppm): 2.74 (s, 6H), 3.48 (s, 3H), 6.95 (s, 1H); 7.09-7.13 (m, 2H), 7.20 (t, 1H), 7.25-7.35 (m, 2H), 7.40 (s, 1H), 8.26 (d, 1H).

$^{19}$F-NMR (282.4 MHz, $CDCl_3$), δ (ppm): −64.81 ($CF_3$).

LC-MS: $t_R$ 3.50 min; m/z=367 [M+H]$^+$. Method A.

Step 4, Procedure 2: Methyl (E)-3-hydroxy-2-[2-[[4-(trifluoromethyl)-2-pyridyl]oxy]phenyl]prop-2-enoate XXII

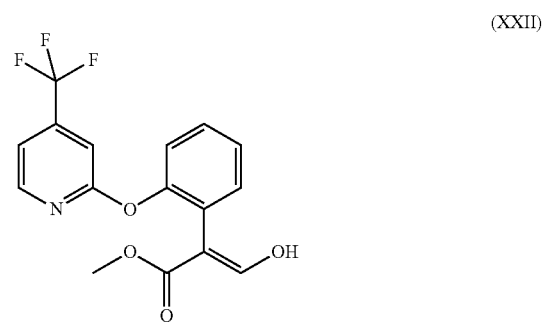 [SMILES: COC(=O)/C(=C/O)c1ccccc1Oc1cc(C(F)(F)F)ccn1]

(XXII)

To a stirred solution of compound 5 (640 mg, 1.74 mmol) in MeOH (18 ml), 2M HCl (9 ml) was added at 0° C. and stirred at room temperature for 20 minutes. The volume of the reaction mixture was reduced by half under reduced pressure. The residue was diluted with water and extracted with ethyl acetate (3×60 ml). The combined organic phases were dried over sodium sulphate, filtered and concentrated to give methyl (E)-3-hydroxy-2-[2-[[4-(trifluoromethyl)-2-pyridyl]oxy]phenyl]prop-2-enoate XXII. Crude yield=555 mg.

Step 5, Procedure 2: Methyl (E)-3-hydroxy-2-[2-[[4-(trifluoromethyl)-2-pyridyl]oxy]phenyl]prop-2-enoate XVIII (XVIII)

To a stirred solution of 555 mg of crude methyl (E)-3-hydroxy-2-[2-[[4-(trifluoromethyl)-2-pyridyl]oxy]phenyl]prop-2-enoate XXII of step 4 (procedure 2) in dry DMF was added $K_2CO_3$ (1.5 eq) dimethyl sulphate (1.2 eq) at 0° C. The mixture was stirred at room temperature for 1 hour and then diluted with water and extracted with ethyl acetate. The combined organic layers were dried ($Na_2SO_4$), filtered and concentrated. The crude was purified by column chromatography using combiflash silica gel column and ethyl acetate-hexane solvent system. The desired product eluted with 12-25% of ethyl acetate-hexane. 365 mg (1.03 mmol, 59% over 2 steps) of methyl (E)-3-hydroxy-2-[2-[[4-(trifluoromethyl)-2-pyridyl]oxy]phenyl]prop-2-enoate XVIII were obtained.

$^1$H-NMR (400 MHz, $CDCl_3$), δ (ppm): 3.56 (s, 3H), 3.70 (s, 3H), 6.99 (s, 1H); 7.12-7.20 (m, 2H), 7.25-7.41 (m, 3H), 7.42 (s, 1H), 8.32 (d, 1H).

$^{19}$F-NMR (282.4 MHz, CDCl$_3$), δ (ppm): −64.82 (CF$_3$).

LC-MS: t$_R$ 3.72 min; m/z=354 [M+H]$^+$. Method A (Epic c18 4.6×50, 5u)

GC-MS: t$_R$ 7.27 min; m/z=353 [M]$^+$. Method B.

BIOLOGY EXAMPLES

Example B1: *Aedes aegypti* (Yellow Fever Mosquito)

The individual wells of a twelve (12) well tissue culture plates were treated with 100 μl of an ethanol solution containing a test compound at 2 ppm and 0.2 ppm concentration. Once the deposits were dry, five non-blood fed adult female *Aedes aegypti* (between two to five day old) were added to each well, and sustained with a 10% sucrose solution in a cotton wool plug. Assessment of the knockdown was carried our after 1 hour, and mortality after 24 hours and 48 hours. Results are shown in Tables B1.

TABLES B1

| | Compound of formula I | | | | Compound of formula II | | |
|---|---|---|---|---|---|---|---|
| | adult knockdown | adult mortality | | | adult knockdown | adult mortality | |
| ppm | 1 h | 24 h | 48 h | ppm | 1 h | 24 h | 48 h |
| 20 | 100 | 100 | 100 | 20 | 100 | 100 | 100 |
| 2 | 20 | 60 | 80 | 2 | 0 | 0 | 0 |
| 0.2 | 0 | 20 | 20 | 0.2 | 0 | 0 | 0 |

Example B2: *Anopheles stephensi* (Indian Malaria Mosquito)

The individual wells of a twelve (12) well tissue culture plates were treated with 100 μl of an ethanol solution containing a test compound at 2 ppm and 0.2 ppm concentration. Once the deposits were dry, five non-blood fed adult female *Anopheles stephensi* (between two to five day old) were added to each well, and sustained with a 10% sucrose solution in a cotton wool plug. Assessment of the knockdown was carried our after 1 hour, and mortality after 24 hours and 48 hours. Results are shown in Tables B2.

TABLES B2

| | Compound of formula I | | | | Compound of formula II | | |
|---|---|---|---|---|---|---|---|
| | adult knockdown | adult mortality | | | adult knockdown | adult mortality | |
| ppm | 1 h | 24 h | 48 h | ppm | 1 h | 24 h | 48 h |
| 20 | 100 | 100 | 100 | 20 | 100 | 100 | 100 |
| 2 | 80 | 100 | 100 | 2 | 0 | 80 | 100 |
| 0.2 | 0 | 20 | 20 | 0.2 | 0 | 0 | 0 |

Example B3: *Anopheles stephensi*

The individual wells of six (6) well tissue culture plates were treated with 250 μl of an ethanol solution containing a test compound at a defined concentration. Once the deposits were dry, ten non-blood fed adult female *Anopheles stephensi* (each between two to five day old) were added to each well, and sustained with a 10% sucrose solution in a cotton wool plug. Assessment of the knockdown was carried our after 1 hour, and mortality after 24 hours and 48 hours. Each treatment was replicated twice, with the mean mortality recorded. Results are shown in Tables B3:

TABLES B3

| | Compound of formula I | | | | Compound of formula II | | |
|---|---|---|---|---|---|---|---|
| Rate | Knockdown | Mortality | | Rate | Knockdown | Mortality | |
| ppm | 1 h | 24 h | 48 h | ppm | 1 h | 24 h | 48 h |
| 2.5 | 87 | 100 | 100 | 2.5 | 73 | 93 | 97 |
| 1.25 | 70 | 98 | 100 | 1.25 | 48 | 83 | 88 |
| 0.625 | 43 | 80 | 82 | 0.625 | 27 | 33 | 30 |
| 0.3125 | 20 | 63 | 65 | 0.3125 | 13 | 15 | 22 |

Example B4: Bottle Based Cross Resistance Study

Based on the "CDC bottle assay" (described at http://www.cdc.gov/malaria/resources/pdf/fsp/ir_manual/ir_cdc_bioassay_en.pdf) 1 ml of ethanol containing a test compound at a defined concentration was added to a 250 ml glass bottle and the bottles were placed on a rolling table to coat the inner surfaces as the solvent evaporated. Once dry, twenty five non-blood fed adult female mosquitoes of the appropriate species and strains (each three day old) were aspirated from the stock culture and gently blown into the exposure bottles. The lid of the bottle was replaced and the bottle placed upright out of direct sun light under standard culture conditions, nominally 26° C. and 60-80% relative humidity.

A stopwatch was started, and the assessment of the knock-down were made after 15 mins and 60 minutes. A mosquito was said to be knocked down if it was unable to stand, following the CDC definition. The bottles were replaced in an upright position when not being assessed.

After one hour the mosquitoes were carefully removed from the bottle with an aspirator and placed in a recovery cup. The mosquitoes were supplied with a 10% sucrose solution on a cotton wool bung, and stored under culture conditions. Assessments of the mortality were made after 24 hours.

Each treatment was replicated a minimum of three times, with the exception of the Banfora strain, where only a single replicate was undertaken, with the mean knockdown or mortality recorded. In each study, a set of bottles was infested with a known insecticide susceptible strain of mosquitoes from the same genera as the resistant strains. Results are shown in Table B4.

TABLE B4

| | Rate ppm | Compound of formula I | Compound of formula II | Permethrin |
|---|---|---|---|---|
| VK7 2014 | 25 | 100 | 100 | 7 |
| | 12.5 | 61 | 18 | 3 |
| | 6.25 | 10 | 7 | 5 |
| Tiassalé 13 | 25 | 100 | 100 | 69 |
| | 12.5 | 81 | 46 | 45 |
| | 6.25 | 69 | 55 | 13 |
| Banfora | 25 | 100 | 100 | 45 |
| | 12.5 | 52 | 33 | 38 |
| | 6.25 | 26 | 13 | 14 |
| Kisumu sus | 25 | 100 | 100 | |
| | 12.5 | 99 | 33 | |
| | 6.25 | 74 | 61 | |
| | 20 | | | 100 |
| | 10 | | | 100 |

TABLE B4-continued

| | 5 | | 100 |
|---|---|---|---|
| Name | Species | Country of origin | Phenotype |
| Kisumu | Anopheles gambiae | Kenya | Susceptible |
| Banfora | An. gambiae | Burkina Faso | DDT & pyrethroid resistant |
| VK7 2014 | An. coluzzii | Burkina Faso | DDT & pyrethroid resistant |
| Tiassale 13 | An. gambiae | Cote d'Ivoire | Pyrethroid resistant |

The invention claimed is:

1. A compound of formula I

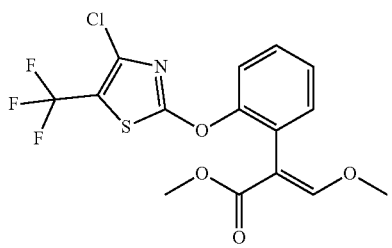

(I)

or a geometric isomer, a salt, or a N-oxide thereof.

2. A method of vector control, comprising: applying the compound of formula I as defined in claim 1 to the vector or locus thereof.

3. A vector control management product comprising the compound of formula I as defined in claim 1.

4. The product according to claim 3 wherein the product is a net.

5. The product according to claim 3, wherein the product is a composition for coating a net.

6. The product according to claim 3, wherein the product is a composition for spraying surfaces of a dwelling.

7. The product according to claim 1, wherein a further insecticide and/or synergist is present.

8. A polymeric material incorporated with a compound of formula I as defined in claim 1, which material is useful for making substrate or non-living material, threads, fibres, yarns, pellets, nets and weaves.

9. A kit for treating a thread, fibre, yarn, net and weave by coating wash resistant insecticidal properties thereto comprising: a first sachet comprising a pre-measured amount of the compound of formula I as defined in claim 1, and a second sachet comprising a pre-measured amount of at least one polymeric binder.

10. A method for treating a thread, fibre, yarn, net and weave by coating wash resistant insecticidal properties thereto comprising (i) preparing a treatment composition, which comprises the compound of formula I as defined in claim 1, (ii) treating said thread, fibre, yarn, net and weave and (iii) drying the resulting treated thread, fibre, yarn, net and weave.

11. A method of preparing a polymeric material impregnated with a compound of formula I as defined in claim 1, which material is useful for making substrate or non-living material, threads, fibres, yarns, pellets, nets and weaves, which method comprises mixing a polymer with the compound of formula I as defined in claim 1 at a temperature between 120 to 250° C.

12. A method for mosquito vector-control, controlling mosquito vectors carrying pathogenic disease, which method comprises (a) applying an effective amount of a liquid composition comprising the compound of formula I as defined in claim 1, and a polymeric binder, and optionally, one or more other insecticides, and/or synergists, to a surface of a dwelling; and/or (b) placing a substrate or non-living material incorporated with the compound of formula I as defined in claim 1, and optionally an additive, one or more other insecticides, and/or synergists, within a dwelling.

13. A net incorporated with the compound of formula I as defined in claim 1.

14. A net according to claim 13 having a biological activity in accordance with the WHOPES guidelines of a knockdown after 60 minutes of between 95 percent and 100 percent and/or a mortality after 24 hours of between 80 percent and 100 percent after 20 washes.

15. A process for making a compound for formula I as defined in claim 1 comprising
   a. reacting the thiazole compound III containing a leaving group LG1 under basic conditions with the phenol compound IV in a solvent in the presence of an amine catalyst between 0° C. and the boiling point of the solvent;

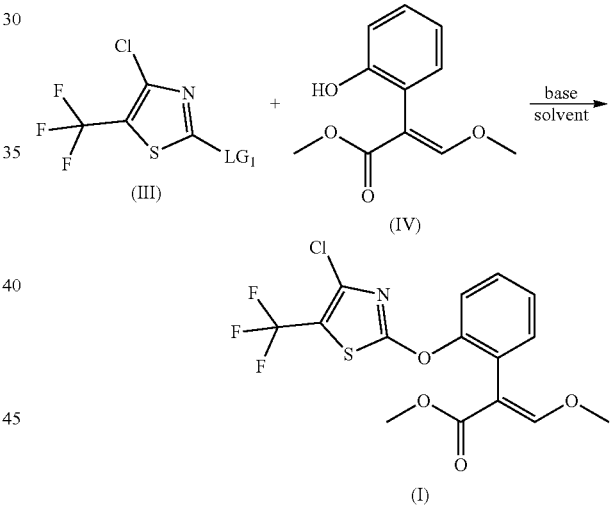

or
   b. treating the acetal compound V with an acid in the presence of acetic anhydride in a solvent between 0° C. and the boiling point of the used solvent.

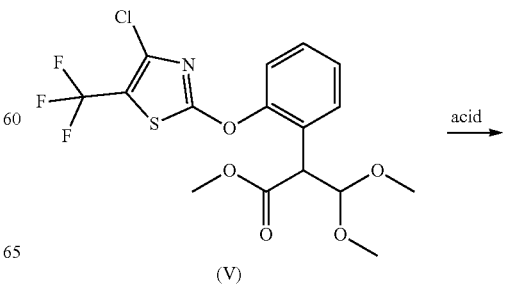

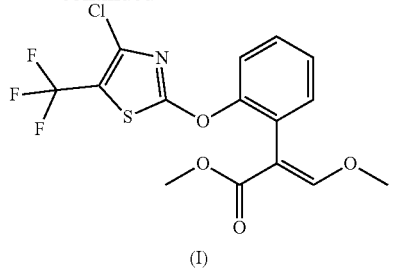

(I)

16. A compound of the formulae V or XII

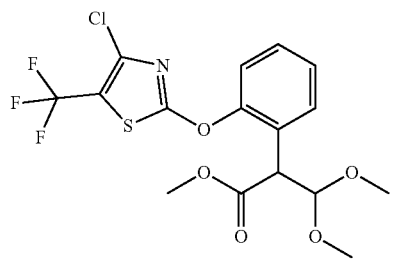

(V)

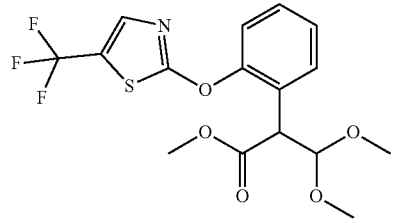

(XII)

or a geometric isomer, or salt, or a N-oxide thereof.

17. The compound of claim 16, wherein the compound is the compound of the formulae V.

18. The compound of claim 16, wherein the compound is the compound of the formulae XII.

19. The method of claim 2, wherein the applying is to the vector.

20. The method of claim 17, wherein the vector is a mosquito.

21. The method of claim 2, further comprising identifying the locus of potential or known interaction between the vector and a mammal.

* * * * *